United States Patent [19]

Braig et al.

[11] Patent Number: 5,612,093
[45] Date of Patent: Mar. 18, 1997

[54] TITANIUM AND ZIRCONIUM COMPLEXES OF CARBOXYLIC ACIDS AS CORROSION INHIBITORS

[75] Inventors: Adalbert Braig, Binzen, Germany; Markus Frey, Marly; Andreas Kramer, Düdingen, both of Switzerland

[73] Assignee: Ciba-Geigy Corporation, Tarrytown, N.Y.

[21] Appl. No.: 491,333

[22] Filed: Jun. 30, 1995

[30] Foreign Application Priority Data

Jul. 1, 1994 [CH] Switzerland .............................. 2118/94

[51] Int. Cl.$^6$ ...................................................... B05D 3/02
[52] U.S. Cl. .................. 427/386; 106/14.13; 106/14.41; 252/388; 252/394; 252/396; 427/388.2; 427/388.3; 427/388.4; 524/398; 556/51
[58] Field of Search .............................. 106/14.13, 14.41, 106/14.42; 252/388, 394, 396; 427/386, 388.2, 388.3, 388.4; 524/398; 556/51

[56] References Cited

U.S. PATENT DOCUMENTS

| 4,243,416 | 1/1981 | Grourke et al. ..................... 106/14.13 |
| 4,243,417 | 1/1981 | Grourke et al. ..................... 106/14.13 |
| 4,612,378 | 9/1986 | Bosshard et al. ...................... 548/170 |
| 4,909,987 | 3/1990 | Penninger et al. ........................ 422/17 |
| 5,391,240 | 2/1995 | Seidel et al. ............................ 148/256 |
| 5,458,678 | 10/1995 | Armstrong et al. ................ 106/14.41 |

FOREIGN PATENT DOCUMENTS

| 0234649 | 9/1987 | European Pat. Off. . |
| 0412933 | 2/1991 | European Pat. Off. . |
| 0496555 | 7/1992 | European Pat. Off. . |
| 0554023 | 8/1993 | European Pat. Off. . |
| 0619290 | 10/1994 | European Pat. Off. . |
| 4120344 | 1/1992 | Germany . |
| 1295432 | 11/1972 | United Kingdom . |
| 1514361 | 6/1978 | United Kingdom . |
| 2258464 | 2/1993 | United Kingdom . |
| 9206226 | 4/1992 | WIPO . |

OTHER PUBLICATIONS

Chem. Abst. 116: 185178u of De 4,120,334, 1992.
J.R. Merchant et al., J. Chem. Soc. Perkin Trans. I, 7, 932–935 (1972).
Dictionary of Organic Compounds, 5th Edition, vol. 4, p. 4152 (1982).
Chem. Abst. 86–160430125 ab. JP. 1095–044–A, May 13, 1986.
Chem. Abst. 120:44426.
J. Bangladesh, Chem. Soc. 6(1), 103–7 (1993).
Chem. Abst. 99:63186 Bilinski, Halka et al. Croat. Chem. Acta 56(1), 53–9 (1983).
Chem. Abst. 98:209055, Aspandiyarova et al, Izu. Akad Nauk Kaz, SSR Ser. Khim (2), 76–78 (1983).

*Primary Examiner*—Michael Lusignan
*Attorney, Agent, or Firm*—David R. Crichton

[57] ABSTRACT

Titanium and zirconium complexes of compounds of the formula I

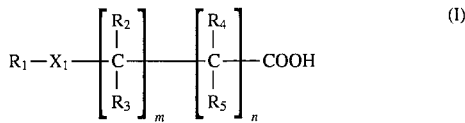

in which the general symbols are as defined in claim 1, are described as corrosion inhibitors in coating compositions for protecting metallic surfaces.

24 Claims, No Drawings

TITANIUM AND ZIRCONIUM COMPLEXES OF CARBOXYLIC ACIDS AS CORROSION INHIBITORS

The present invention relates to coating compositions comprising an organic film-forming binder, preferably a surface-coating material, and titanium complexes or zirconium complexes of carboxylic acids as corrosion inhibitors, the use thereof in coating compositions for protecting metallic surfaces, and novel titanium and zirconium complexes of carboxylic acids.

The use of alkali metal, ammonium and amine salts of carboxylic acids as corrosion inhibitors in aqueous systems is known and is described, for example, in U.S. Pat. No. 4 909 987, EP-A-412 933, EP-A-496 555 or EP-A-554 023.

The use of various metal salts and complexes as corrosion inhibitors is known and is described, for example, in U.S. Pat. No. 4 243 416 and U.S. Pat. No. 4 243 417.

It has now been found that the sparingly water-soluble titanium or zirconium complexes of carboxylic acids are particularly suitable as corrosion inhibitors in coating compositions for protecting metallic surfaces.

The present invention therefore relates to coating compositions comprising a) an organic film-forming binder and b) as a corrosion inhibitor, at least one titanium or zirconium complex of a compound of the formula I

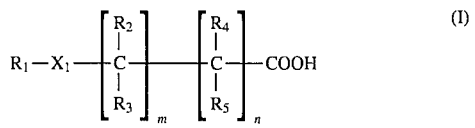

in which $R_1$ is hydrogen, $C_1$–$C_{25}$alkyl, $C_2$–$C_{25}$alkyl which is interrupted by oxygen, sulfur or >N—$R_6$; $C_2$–$C_{24}$alkenyl, $C_4$–$C_{15}$cycloalkyl which is unsubstituted or substituted by $C_1$–$C_4$alkyl; $C_5$–$C_{15}$cycloalkenyl which is unsubstituted or substituted by $C_1$–$C_4$alkyl; $C_{13}$–$C_{26}$polycycloalkyl, $C_7$–$C_9$phenylalkyl which is unsubstituted or substituted on the phenyl ring by $C_1$–$C_4$alkyl; —$COR_7$, a 5- or 6-membered heterocyclic ring which is unsubstituted or substituted by $C_1$–$C_4$alkyl, $C_1$–$C_4$alkoxy, halogen or carboxyl; a benzo-fused 5- or 6-membered heterocyclic ring which is unsubstituted or substituted by $C_1$–$C_4$alkyl, $C_1$–$C_4$alkoxy, halogen or carboxyl; or $R_1$ furthermore is a radical of the formula II, III or IV

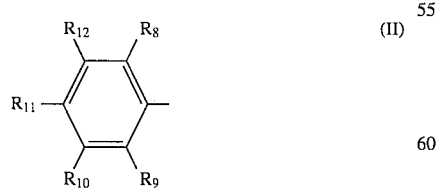

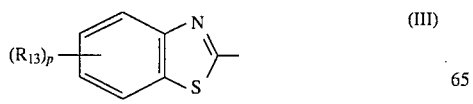

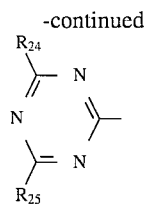

$R_2$, $R_3$, $R_4$ and $R_5$ independently of one another are hydrogen, hydroxyl, $C_1$–$C_{18}$alkoxy, $C_2$–$C_{18}$alkoxy which is interrupted by oxygen, sulfur or >N—$R_6$;

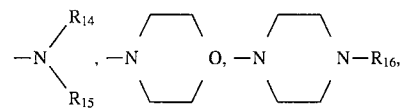

$C_1$–$C_{25}$alkyl, $C_2$–$C_{25}$alkyl which is interrupted by oxygen, sulfur or >N—$R_6$; $C_2$–$C_{24}$alkenyl, $C_5$–$C_{15}$cycloalkyl which is unsubstituted or substituted by $C_1$–$C_4$alkyl; $C_5$–$C_{15}$cycloalkenyl which is unsubstituted or substituted by $C_1$–$C_4$alkyl; phenyl or naphthyl which are unsubstituted or substituted by $C_1$–$C_4$alkyl; $C_7$–$C_9$phenylalkyl which is unsubstituted or substituted on the phenyl ring by $C_1$–$C_4$alkyl; $C_{10}$–$C_{12}$naphthylalkyl which is unsubstituted or substituted on the naphthyl ring by $C_1$–$C_4$alkyl; or —$COR_7$, with the proviso that if one of the radicals $R_2$, $R_3$, $R_4$ or $R_5$ is hydroxyl,

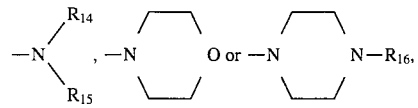

the other radical bonded to the same C atom is other than hydroxyl,

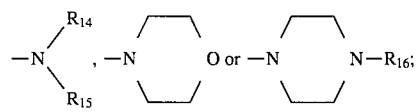

or $R_2$ and $R_3$ or $R_4$ and $R_5$ furthermore, together with the C atom to which they are bonded, form a $C_5$–$C_{12}$cycloalkylidene ring which is unsubstituted or substituted by $C_1$–$C_4$alkyl, $R_6$ is hydrogen or $C_1$–$C_8$alkyl, $R_7$ is hydroxyl, $C_1$–$C_{18}$alkoxy, $C_2$–$C_{18}$alkoxy, $C_2$–$C_{18}$alkoxy which is interrupted by oxygen, sulfur or

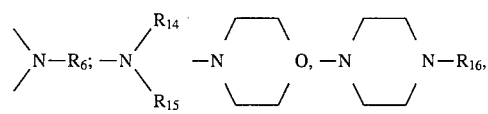

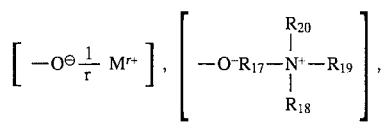

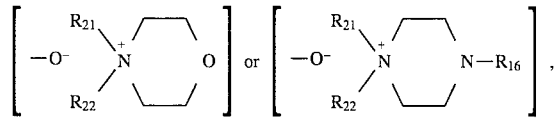

$R_8$, $R_9$, $R_{10}$, $R_{11}$ and $R_{12}$ independently of one another are hydrogen, hydroxyl, halogen, nitro,

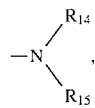

cyano, $CF_3$, —$COR_7$, $C_1$–$C_{25}$alkyl, $C_1$–$C_{25}$alkyl which is interrupted by oxygen, sulfur or >N—$R_6$; $C_1$–$C_{25}$halogenoalkyl, $C_1$–$C_{18}$alkoxy, $C_2$–$C_{18}$alkoxy which is interrupted by oxygen, sulfur or >N—$R_6$; $C_1$–$C_{18}$alkylthio, $C_2$–$C_{24}$alkenyl, $C_5$–$C_{15}$cycloalkyl which is unsubstituted or substituted by $C_1$–$C_4$alkyl; $C_5$–$C_{15}$cycloalkenyl which is unsubstituted or substituted by $C_1$–$C_4$alkyl; phenyl or naphthyl which are unsubstituted or substituted by $C_1$–$C_4$alkyl; $C_7$–$C_9$phenylalkyl which is unsubstituted or substituted on the phenyl ring by $C_1$–$C_4$alkyl; $C_{10}$–$C_{12}$naphthylalkyl which is unsubstituted or substituted on the naphthyl ring by $C_1$–$C_4$alkyl; phenoxy or naphthoxy which are unsubstituted or substituted by $C_1$–$C_4$alkyl; $C_7$–$C_9$-phenylalkoxy which is unsubstituted or substituted on the phenyl ring by $C_1$–$C_4$alkyl; $C_{10}$–$C_{12}$naphthylalkoxy which is unsubstituted or substituted on the naphthyl ring by $C_1$–$C_4$alkyl; or the radicals $R_9$ and $R_{10}$ or the radicals $R_{10}$ and $R_{11}$ or the radicals $R_{11}$ and $R_{12}$ or the radicals $R_8$ and $R_{12}$ furthermore, together with the carbon atoms to which they are bonded, form a benzo ring which is unsubstituted or substituted by $C_1$–$C_4$alkyl, halogen or $C_1$–$C_4$alkoxy, $R_{13}$ is hydrogen, hydroxyl, halogen, nitro, cyano, $CF_3$, $C_1$–$C_{25}$alkyl, $C_2$–$C_{25}$alkyl which is interrupted by oxygen, sulfur or >N—$R_6$, $C_1$–$C_{25}$halogenoalkyl, $C_1$–$C_{18}$alkoxy, $C_2$–$C_{18}$alkoxy which is interrupted by oxygen, sulfur or >N—$R_6$; $C_1$–$C_{18}$alkylthio or $C_2$–$C_{24}$alkenyl;

$R_{14}$ and $R_{15}$ independently of one another are hydrogen, $C_1$–$C_{25}$alkyl, $C_2$–$C_{25}$alkyl which is interrupted by oxygen, sulfur or >N—$R_6$; $C_2$–$C_{24}$alkenyl, $C_5$–$C_{15}$cycloalkyl which is unsubstituted or substituted by $C_1$–$C_4$alkyl; phenyl or naphthyl which are unsubstituted or substituted by $C_1$–$C_4$alkyl, $R_{16}$ is hydrogen or $C_1$–$C_{18}$alkyl, $R_{17}$, $R_{18}$, $R_{19}$, $R_{20}$, $R_{21}$ and $R_{22}$ independently of one another are hydrogen or $C_1$–$C_{25}$alkyl, $R_{23}$ is hydrogen, $C_1$–$C_{25}$alkyl, $C_2$–$C_{25}$alkyl which is interrupted by oxygen, sulfur or >N—$R_6$; $C_2$–$C_{24}$alkenyl, $C_5$–$C_{15}$cycloalkyl which is unsubstituted or substituted by $C_1$–$C_4$alkyl; phenyl or naphthyl which are unsubstituted or substituted by $C_1$–$C_4$alkyl, $R_{24}$ and $R_{25}$ independently of one another are hydrogen, $C_1$–$C_{25}$alkyl, $C_1$–$C_{18}$alkoxy, —$X_2$—$(CH_2)_sCOR_7$ or

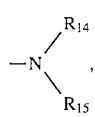

M is an r-valent metal cation, $X_1$ is a direct bond, oxygen, sulfur, —$NR_{23}$—, $C_1$–$C_{18}$alkylene, $C_2$–$C_{18}$alkylene which is interrupted by oxygen, sulfur or >N—$R_6$, $C_2$–$C_{18}$alkenylene, $C_2$–$C_{18}$alkynylene, $C_2$–$C_{20}$alkylidene, $C_7$–$C_{20}$phenylalkylidene or $C_5$–$C_8$cycloalkylene, with the proviso that if m and n are 0, $X_1$ is other than oxygen and sulfur, $X_2$ is oxygen or —$NR_{23}$—, m and n independently of one another are an integer from 0 to 10, p is an integer from 0 to 4, r is 1, 2 or 3, and s is an integer from 1 to 8.

Alkyl having up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5, 5-hexamethylhexyl, tridecyl, tetradecyl, pentadecyl, hexadecyl, heptadecyl, octadecyl, eicosyl or docosyl. $R_1$, $R_2$, $R_3$, $R_4$, $R_5$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$ and $R_{23}$ are preferably, for example, $C_1$–$C_{18}$alkyl, in particular $C_1$–$C_{12}$alkyl, for example $C_1$–$C_8$alkyl. $R_{10}$ and $R_{12}$ are particularly preferably, for example, $C_1$–$C_8$alkyl, in particular $C_1$–$C_4$alkyl, for example tert-butyl.

Alkyl having 2 to 25 carbon atoms which is interrupted by oxygen, sulfur or >N—$R_6$ can be interrupted once or several times and is, for example, $CH_3$—O—$CH_2$—, $CH_3$—S—$CH_2$—, $CH_3$—NH—$CH_2$—, $CH_3$—N($CH_3$)—$CH_2$—, $CH_3$—O—$CH_2CH_2$—O—$CH_2$—, $CH_3$—(O—$CH_2CH_2$—)$_2$O—$CH_2$—, $CH_3$—(O—$CH_2CH_2$—)$_3$O—$CH_2$— or $CH_3$—(O—$CH_2CH_2$—)$_4$O—$CH_2$—. $R_1$, $R_2$, $R_3$, $R_4$, $R_5$, $R_8$, $R_9$, $R_{10}$, $R_{11}$, $R_{12}$, $R_{13}$, $R_{14}$, $R_{15}$ and $R_{23}$ are particularly preferably, for example, $C_2$–$C_{18}$alkyl which is interrupted by oxygen, in particular $C_4$–$C_{18}$alkyl which is interrupted by oxygen, for example $C_4$–$C_{12}$alkyl which is interrupted by oxygen.

Alkenyl having 2 to 24 carbon atoms is a branched or unbranched radical, for example vinyl, propenyl, 2-butenyl, 3-butenyl, isobutenyl, n-2,4-pentadienyl, 3-methyl-2-butenyl, n-2-octenyl, n-2-dodecenyl, iso-dodecenyl, oleyl, n-2-octadecenyl or n-4-octadecenyl. $R_1$, $R_2$, $R_3$, $R_4$, $R_5$, $R_8$, $R_9$, $R_{10}$, $R_{11}$, $R_{12}$, $R_{13}$, $R_{14}$, $R_{15}$ and $R_{23}$ are particularly preferably alkenyl having 3 to 18, in particular 3 to 12, for example 3 to 10, carbon atoms.

$C_4$–$C_{15}$Cycloalkyl which is unsubstituted or substituted by $C_1$–$C_4$alkyl, in particular $C_5$–$C_{15}$cycloalkyl which preferably contains 1 to 3, in particular 1 or 2, branched or unbranched alkyl group radicals, is, for example, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl, cyclooctyl or cyclododecyl. $R_1$ is preferably, for example, the $C_4$–$C_{12}$cycloalkyl radicals occurring in naphthenic acid [J. Buckingham, Dictionary of Organic Compounds, Volume 4, page 4152, 5th Edition (1982)]. $R_2$, $R_3$, $R_4$, $R_5$, $R_8$, $R_9$, $R_{10}$, $R_{11}$, $R_{12}$, $R_{14}$, $R_{15}$ and $R_{23}$ are particularly preferably $C_5$–$C_{12}$cycloalkyl, in particular $C_5$–$C_9$cycloalkyl, for example cyclohexyl.

$C_5$–$C_{15}$Cycloalkenyl which is unsubstituted or substituted by $C_1$–$C_4$alkyl and preferably contains 1 to 3, in particular 1 or 2, branched or unbranched alkyl group radicals is, for example, cyclopentenyl, methylcyclopentenyl, dimethylcyclopentenyl, cyclohexenyl, methylcyclohexenyl, dimethylcyclohexenyl, trimethylcyclohexenyl, tert-butylcyclohexenyl, cycloheptenyl, cyclooctenyl or cyclododecenyl. $C_5$–$C_{12}$Cycloalkenyl is preferred, in particular $C_5$–$C_8$cycloalkenyl, for example cyclohexenyl.

$C_{13}$–$C_{26}$Polycycloalkyl is, for example, the $C_{13}$–$C_{26}$polycycloalkyl radicals occurring in naphthenic acid [J. Buckingham, Dictionary of Organic Compounds, Volume 4, page 4152, 5th Edition (1982)].

$C_7$–$C_9$Phenylalkyl which is unsubstituted or substituted on the phenyl radical by $C_1$–$C_4$alkyl and preferably contains 1 to 3, in particular 1 or 2, branched or unbranched alkyl group radicals is, for example, benzyl, α-methylbenzyl, α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tert-butylbenzyl. Benzyl is preferred.

A 5- or 6-membered heterocyclic ring which is unsubstituted or substituted by $C_1$–$C_4$alkyl, $C_1$–$C_4$alkoxy, halogen or carboxyl and preferably contains 1 to 3, in particular 1 or 2, branched or unbranched alkyl or alkoxy group radicals and preferably 1 to 3, in particular 1 or 2, hetero atoms from the group consisting of nitrogen, oxygen and sulfur is, for example, thienyl, 2-methylthienyl, 3-chlorothienyl, 3-methoxythienyl, tetrahydrofuranyl, furyl, pyrrolidinyl, 1-methylpyrrolidinyl, pyrrolyl, thiazolyl, isothiazolyl, imidazolyl, carboxyimidazolyl, triazolyl, tetrazolyl, oxazolyl, isoxazolyl, pyridyl, piperidinyl, morpholinyl, pyrazinyl, carboxypyrazinyl, piperazinyl, triazinyl or 2,6-dimethoxytriazonyl.

A benzo-fused 5- or 6-membered heterocyclic ring which is unsubstituted or substituted by $C_1$–$C_4$alkyl, $C_1$–$C_4$alkoxy, halogen or carboxyl and preferably contains 1 to 3, in particular 1 or 2, branched or unbranched alkyl or alkoxy group radicals and preferably 1 to 3, in particular 1 or 2, hetero atoms from the group consisting of nitrogen, oxygen and sulfur is, for example, benzothiazolyl, 5-chlorobenzothiazolyl, 5-methoxybenzothiazolyl, 5-methylbenzothiazolyl, benzimidazolyl, benzoxazolyl, benzisothiazolyl or benzothienyl.

Alkoxy having up to 18 carbon atoms is a branched or unbranched radical, for example methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy. $C_1$–$C_{12}$Alkoxy is preferred, in particular $C_1$–$C_{10}$alkoxy, for example $C_1$–$C_8$alkoxy.

$C_2$–$C_{18}$Alkoxy which is interrupted by oxygen, sulfur or >N—$R_6$ is, for example, $CH_3$—O—$CH_2CH_2$O—, $CH_3$—S—$CH_2CH_2$O—, $Ch_3$—NH—$CH_2CH_2$O—, $CH_3$—N($CH_3$)—$CH_2CH_2$O—, $CH_3$—O—$CH_2CH_2$—O—$CH_2CH_2$O—, $CH_3$—(O—$CH_2CH_2$—)$_2$O—$CH_2CH_2$O—, $CH_3$—(O—$CH_2CH_2$—)$_3$O—$CH_2CH_2$O— or $CH_3$—(O—$CH_2CH_2$—)$_4$O—$CH_2CH_2$O—.

Phenyl or naphthyl which are substituted by $C_1$–$C_4$alkyl and preferably contain 1 to 3, in particular 1 or 2, alkyl groups are, for example, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl, 2,6-diethylphenyl, 1-methylnaphthyl, 2-methylnaphthyl, 4-methylnaphthyl, 1,6-dimethylnaphthyl or 4-tert-butylnaphthyl.

$C_{10}$–$C_{12}$Naphthylalkyl which is unsubstituted or substituted on the naphthyl ring by $C_1$–$C_4$alkyl and preferably contains 1 to 3, in particular 1 or 2, branched or unbranched alkyl group radicals is, for example, naphthylmethyl, α-methylnaphthylmethyl, α,α-dimethylnaphthylmethyl, naphthylethyl, 2-methyl-1-naphthylmethyl, 3-methyl-1-naphthylmethyl, 4-methyl-1-naphthylmethyl, 2,4-dimethyl-1-naphthylmethyl, 2,6-dimethyl-1-naphthylmethyl or 4-tert-butyl-1-naphthylmethyl.

A $C_5$–$C_{12}$cycloalkylidene ring which is unsubstituted or substituted by $C_1$–$C_4$alkyl and preferably contains 1 to 3, in particular 1 or 2, branched or unbranched alkyl group radicals is, for example, cyclopentylidene, methylcyclopentylidene, dimethylcyclopentylidene, cyclohexylidene, methylcyclohexylidene, dimethylcyclohexylidene, trimethylcyclohexylidene, tert-butylcyclohexylidene, cyclooctylidene, cyclodecylidene or cyclododecylidene. Cyclohexylidene and tert-butylcyclohexylidene are preferred.

Halogen is, for example, chlorine, bromine or iodine. Chlorine is preferred.

Halogenoalkyl having up to 25 carbon atoms is a branched or unbranched radical, for example chloromethyl, chloroethyl, chloropropyl, chlorobutyl or 3-chloro-1-butyl.

Alkylthio having up to 18 carbon atoms is a branched or unbranched radical, for example methylthio, ethylthio, propylthio, isopropylthio, n-butylthio, isobutylthio, pentylthio, isopentylthio, hexylthio, heptylthio, octylthio, decylthio, tetradecylthio, hexadecylthio or octadecylthio. Alkylthio having 1 to 12, in particular 1 to 8, for example 1 to 6, carbon atoms is preferred.

Phenoxy or naphthoxy which are substituted by $C_1$–$C_4$alkyl and preferably contain 1 to 3, in particular 1 or 2, alkyl groups are, for example, o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy, 2,6-diethylphenoxy, 1-methylnaphthoxy, 2-methylnaphthoxy, 4-methylnaphthoxy, 1,6-dimethylnaphthoxy or 4-tert-butylnaphthoxy.

$C_7$–$C_9$Phenylalkoxy which is unsubstituted on the phenyl ring the phenyl ring by $C_1$–$C_4$alkyl and preferably contains 1 to 3, in particular 1 or 2, branched or unbranched alkyl group radicals is, for example, benzyloxy, 2-phenylethoxy, 2-methylbenzyloxy, 3-methylbenzyloxy, 4-methylbenzyloxy, 2,4-dimethylbenzyloxy, 2,6-dimethylbenzyloxy or 4-tert-butylbenzyloxy. Benzyloxy is preferred.

$C_{10}$–$C_{12}$Naphthylalkoxy which is unsubstituted or substituted on the naphthyl ring by $C_1$–$C_4$alkyl and preferably contains 1 to 3, in particular 1 or 2, branched or unbranched alkyl group radicals is, for example, naphthylmethoxy, naphthylethoxy, 2-methyl-1-naphthylmethoxy, 3-methyl-1-naphthylmethoxy, 4-methyl-1-naphthylmethoxy, 2,4-dimethyl-1-naphthylmethoxy, 2,6-dimethyl-1-naphthylmethoxy or 4-tert-butyl-1-naphthylmethoxy.

A mono-, di- or trivalent metal cation is preferably an alkali metal, alkaline earth metal or aluminium cation, for example $Na^+$, $K^+$, $Mg^{++}$, $Ca^{++}$ or $Al^{+++}$.

$C_1$–$C_{18}$Alkylene is a branched or unbranched radical, for example methylene, ethylene, propylene, tetramethylene, pentamethylene, hexamethylene, heptamethylene, octamethylene, decamethylene, dodecamethylene or octadecamethylene. $X_1$ is preferably, for example, $C_1$–$C_{12}$alkylene, in particular $C_1$–$C_{10}$alkylene, for example $C_1$–$C_8$alkylene.

$C_2$–$C_{18}$Alkylene which is interrupted by oxygen, sulfur or >N—$R_6$ can be interrupted once or several times and is, for example, —$CH_2$—O—$CH_2$—, —$CH_2$—S—$CH_2$—, —$CH_2$—NH—$CH_2$—, —$CH_2$—N($CH_3$)—$CH_2$—, —$CH_2$—O—$CH_2CH_2$—O—$CH_2$—, —$CH_2$—(O—$CH_2CH_2$—)$_2$O—$CH_2$—, —$CH_2$—(O—$CH_2CH_2$—)$_3$O—$CH_2$—, —$CH_2$—(O—$CH_2CH_2$—)$_4$O—$CH_2$— or —$CH_2CH_2$—S—$CH_2CH_2$—. $X_1$ is preferably, for example, $C_2$–$C_{18}$alkylene which is interrupted by oxygen, in particular $C_4$–$C_{18}$alkylene which is interrupted by oxygen, for example $C_4$–$C_{12}$alkylene which is interrupted by oxygen.

$C_2$–$C_{18}$Alkenylene is, for example, vinylene, methylvinylene, octenylethylene or dodecenylethylene. $C_2$–$C_{12}$Alkenylene is preferred, in particular $C_2$–$C_8$alkenylene. $X_1$ is particularly preferably $C_2$–$C_4$alkenylene, in particular vinylene.

$C_2$–$C_{18}$Alkynylene is, for example, —C≡C—, 2-propynylene(—C≡C—$CH_2$—), 2-butynylene(—$CH_2$—C≡C—

$CH_2$—), 2-pentynylene, 2-hexynylene, 3-hexynylene, 3-heptynylene, 2-decynylene, 4-decynylene or 8-octadecynylene. $X_1$ is preferably $C_2$–$C_{12}$alkynylene, in particular $C_2$–$C_8$alkynylene, for example 2-butynylene.

Alkylidene having 2 to 20 carbon atoms is, for example, ethylidene, propylidene, butylidene, pentylidene, 4-methylpentylidene, heptylidene, nonylidene, tridecylidene, nonadecylidene, 1-methylethylidene, 1-ethylpropylidene or 1-ethylpentylidene. $X_1$ is preferably, for example, alkylidene having 2 to 12, in particular 2 to 8, for example 2 to 6, carbon atoms.

Phenylalkylidene having 7 to 20 carbon atoms is, for example, benzylidene, 2-phenylethylidene or 1-phenyl-2-hexylidene. $X_1$ is preferably, for example, phenylalkylidene having 7 to 16, in particular 7 to 12, for example 7 to 9, carbon atoms.

$C_5$–$C_8$Cycloalkylene is a saturated hydrocarbon group having two free valencies and at least one ring unit and is, for example, cyclopentylene, cyclohexylene, cycloheptylene or cyclooctylene. Cyclohexylene is preferred.

Preferred coating compositions are those comprising a titanium or zirconium complex of a compound of the formula I in which, in the case where m and n are 0, $X_1$ is a direct bond and $R_1$ is a radical of the formula II

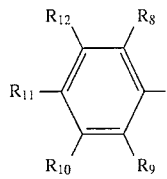
(II)

at least one of the radicals $R_8$, $R_9$, $R_{10}$, $R_{11}$ and $R_{12}$ is other than hydrogen.

Coating compositions which are of interest are those comprising a titanium or zirconium complex of a compound of the formula I in which $R_1$ is hydrogen, $C_1$–$C_{18}$alkyl, $C_2$–$C_{18}$alkyl which is interrupted by oxygen, sulfur or >N—$R_6$; $C_2$–$C_{18}$alkenyl, $C_4$–$C_{15}$cycloalkyl which is unsubstituted or substituted by $C_1$–$C_4$alkyl; $C_5$–$C_{12}$cycloalkenyl which is unsubstituted or substituted by $C_1$–$C_4$alkyl; $C_{13}$–$C_{26}$polycycloalkyl, $C_7$–$C_9$phenylalkyl, —$COR_7$, a 5- or 6- membered heterocyclic ring which is unsubstituted or substituted by $C_1$–$C_4$alkyl, $C_1$–$C_4$alkoxy, chlorine or carboxyl; a benzo-fused 5- or 6-membered heterocyclic ring which is unsubstituted or substituted by $C_1$–$C_4$alkyl, $C_1$–$C_4$alkoxy, chlorine or carboxyl; or $R_1$ furthermore is a radical of the formula II, III or IV

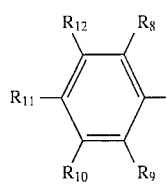
(II)

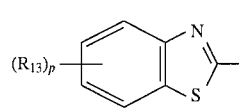
(III)

-continued
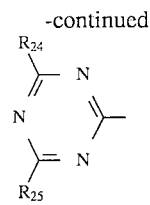
(IV)

$R_2$, $R_3$, $R_4$ and $R_5$ independently of one another are hydrogen, hydroxyl, $C_1$–$C_{12}$alkoxy, $C_2$–$C_{12}$alkoxy which is interrupted by oxygen or sulfur;

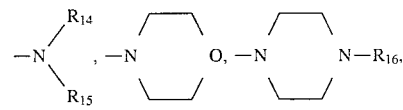

$C_1$–$C_{18}$alkyl, $C_2$–$C_{18}$alkyl which is interrupted by oxygen or sulfur; $C_2$–$C_{18}$alkenyl, $C_5$–$C_{15}$cycloalkyl, $C_5$–$C_{15}$cycloalkenyl, phenyl, naphthyl, $C_7$–$C_9$phenylalkyl, $C_{10}$–$C_{12}$naphthylalkyl or —$COR_7$, with the proviso that if one of the radicals $R_2$, $R_3$, $R_4$ or $R_5$ is hydroxyl,

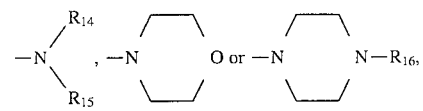

the other radical bonded to the same C atom is other than hydroxyl,

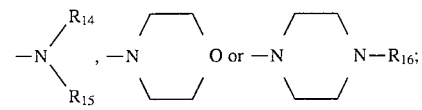

or $R_2$ and $R_3$ or $R_4$ and $R_5$ furthermore, together with the C atom to which they are bonded, form a $C_5$–$C_8$cycloalkylidene ring which is unsubstituted or substituted by $C_1$–$C_4$alkyl, $R_7$ is hydroxyl, $C_1$–$C_{12}$alkoxy, $C_2$–$C_{12}$alkoxy which is interrupted by oxygen or sulfur;

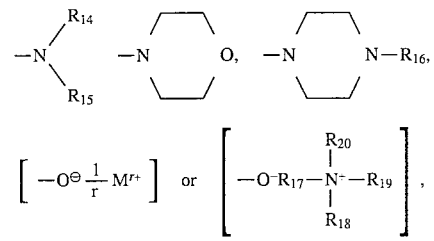

$R_8$, $R_9$, $R_{10}$, $R_{11}$ and $R_{12}$ independently of one another are hydrogen, hydroxyl, halogen, nitro,

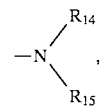

cyano, $CF_3$, —$COR_7$, $C_1$–$C_{18}$alkyl, $C_2$–$C_{18}$alkyl which is interrupted by oxygen or sulfur; $C_1$–$C_{18}$halogenoalkyl, $C_1$–$C_{12}$alkoxy which is interrupted by oxygen or sulfur; $C_1$–$C_{12}$alkylthio, $C_2$–$C_{18}$alkenyl, $C_5$–$C_{12}$cycloalkyl, $C_5$–$C_{12}$cycloalkenyl, phenyl, naphthyl, $C_7$–$C_9$phenylalkyl, $C_{10}$–$C_{12}$naphthylalkyl, phenoxy, naphthoxy, $C_7$–$C_9$phenylalkoxy or $C_{10}$–$C_{12}$naphthylalkoxy; or the radicals $R_9$ and $R_{10}$ or the radicals $R_{10}$ and $R_{11}$ or the radicals $R_{11}$ and $R_{12}$ or the radicals $R_8$ and $R_{12}$ furthermore, together with the carbon atoms to which they are bonded, form a benzo ring which is unsubstituted or substituted by $C_1$–$C_4$alkyl or chlorine, $R_{13}$ is hydrogen, hydroxyl, halogen, nitro, cyano, $CF_3$, $C_1$–$C_{18}$alkyl, $C_2$–$C_{18}$alkyl which is interrupted by oxygen or sulfur; $C_1$–$C_{18}$halogenoalkyl, $C_1$–$C_{12}$alkoxy, $C_2$–$C_{12}$alkoxy which is interrupted by oxygen or sulfur; $C_1$–$C_{12}$alkylthio or $C_2$–$C_{18}$alkenyl, $R_{14}$ and $R_{15}$ independently of one another are hydrogen, $C_1$–$C_{18}$alkyl, $C_2$–$C_{18}$alkyl which is interrupted by oxygen or sulfur; $C_2$–$C_{18}$alkenyl, $C_5$–$C_{12}$cycloalkyl, phenyl or naphthyl, $R_{16}$ is hydrogen or $C_1$–$C_{12}$alkyl, $R_{17}$, $R_{18}$, $R_{19}$, $R_{20}$, $R_{21}$ and $R_{22}$ independently of one another are hydrogen or $C_1$–$C_{18}$alkyl, $R_{23}$ is hydrogen, $C_1$–$C_{18}$alkyl, $C_2$–$C_{18}$alkyl which is interrupted by oxygen or sulfur; $C_2$–$C_{18}$alkenyl, $C_5$–$C_{12}$cycloalkyl, phenyl or naphthyl, $R_{24}$ and $R_{25}$ independently of one another are hydrogen, $C_1$–$C_{18}$alkyl, $C_1$–$C_{12}$alkoxy, —$X_2$—$(CH_2)_sCOR_7$ or

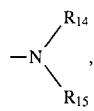

$X_1$ is a direct bond, oxygen, sulfur, —$NR_{23}$—, $C_1$–$C_{12}$alkylene, $C_2$–$C_{12}$alkylene which is interrupted by oxygen or sulfur; $C_2$–$C_{12}$alkenylene, $C_2$–$C_{12}$alkynylene, $C_2$–$C_{16}$alkylidene, $C_7$–$C_{16}$phenylalkylidene or $C_5$–$C_8$cycloalkylene, with the proviso that if m and n are 0, $X_1$ is other than oxygen and sulfur, $X_2$ is —$NR_{23}$—, p is 0, 1 or 2, and s is an integer from 2 to 7.

Preferred coating compositions are those in which, in formula I, $R_1$ is hydrogen, $C_1$–$C_{12}$alkyl, $C_3$–$C_{12}$alkyl which is interrupted by oxygen; $C_2$–$C_{12}$alkenyl, $C_4$–$C_{15}$cycloalkyl, $C_5$–$C_8$cycloalkenyl, $C_{13}$–$C_{26}$polycycloalkyl, benzyl, —$COR_7$, or thienyl, tetrahydrofuranyl, furyl, pyrrolidinyl, pyrrolyl, thiazolyl, isothiazolyl, triazolyl, tetrazolyl, oxazolyl, isoxazolyl, pyridyl, piperidinyl, pyrazinyl, piperazinyl or triazinyl which are unsubstituted or substituted by $C_1$–$C_4$alkyl, $C_1$–$C_4$alkoxy, chlorine or carboxyl or benzo-fused; or $R_1$ furthermore is a radical of the formula II, III or IV

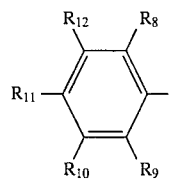

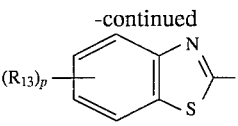

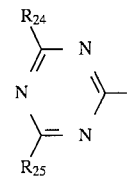

$R_7$ is hydroxyl, $C_1$–$C_{10}$-alkoxy, $C_2$–$C_{12}$ alkoxy which is interrupted by oxygen;

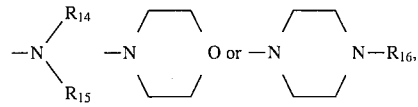

$R_8$, $R_9$, $R_{10}$, $R_{11}$ and $R_{12}$ independently of one another are hydrogen, hydroxyl, chlorine, nitro,

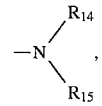

—$COR_7$, $C_1$–$C_{12}$alkyl, $C_2$–$C_{16}$ alkyl which is interrupted by oxygen; $C_1$–$C_{12}$halogenoalkyl, $C_1$–$C_{12}$alkoxy, $C_2$–$C_{12}$alkoxy which is interrupted by oxygen; $C_2$–$C_{12}$alkenyl, $C_5$–$C_9$cycloalkyl, $C_5$–$C_9$cycloalkenyl, phenyl, naphthyl, $C_7$–$C_9$phenylalkyl, $C_{10}$–$C_{12}$naphthylalkyl, phenoxy or $C_7$–$C_9$phenylalkoxy; or the radicals $R_9$ and $R_{10}$ or the radicals $R_{10}$ and $R_{11}$ furthermore, together with the carbon atoms to which they are bonded, form a benzo ring, $R_{13}$ is hydrogen, hydroxyl, chlorine, nitro, $C_1$–$C_{12}$ alkyl, $C_2$–$C_{12}$alkyl which is interrupted by oxygen; $C_1$–$C_{10}$alkoxy or $C_2$–$C_{10}$ alkoxy which is interrupted by oxygen, $R_{14}$ and $R_{15}$ independently of one another are hydrogen, $C_1$–$C_{12}$alkyl, $C_2$–$C_{12}$alkyl which is interrupted by oxygen; $C_5$–$C_9$cycloalkyl or phenyl, $R_{16}$ is hydrogen or $C_1$–$C_8$alkyl, $R_{23}$ is hydrogen, $C_1$–$C_{12}$alkyl, $C_3$–$C_{12}$ alkyl which is interrupted by oxygen; $C_2$–$C_{12}$alkenyl, $C_5$–$C_9$cycloalkyl or phenyl, $R_{24}$ and $R_{25}$ independently of one another are hydrogen or —$X_2$—$(CH_2)_sCOR_7$ or

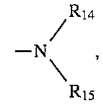

$X_1$ is a direct bond, oxygen, sulfur, —$NR_{23}$—, $C_1$–$C_8$alkylene, $C_2$–$C_8$alkenylene, $C_2$–$C_8$alkynylene, $C_2$–$C_{12}$alkylidene, $C_7$–$C_{12}$phenylalkylidene or $C_5$–$C_8$cycloalkylene, with the proviso that if m and n are 0, $X_1$ is other than oxygen and sulfur, $X_2$ is —$NR_{23}$—, p is 0 or 1, and s is an integer from 3 to 6.

Preferred coating compositions are also those in which, in formula I, $R_2$, $R_3$, $R_4$ and $R_5$ independently of one another are hydrogen, hydroxyl, $C_1$–$C_{10}$alkoxy, $C_2$–$C_{12}$alkoxy which is interrupted by oxygen;

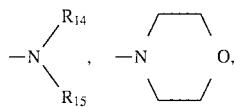

$C_1$–$C_{12}$alkyl, $C_2$–$C_{18}$alkyl which is interrupted by oxygen; $C_2$–$C_{12}$alkenyl, $C_5$–$C_9$cycloalkyl, $C_5$–$C_9$cycloalkenyl, phenyl, naphthyl, $C_7$–$C_9$phenylalkyl or —$COR_7$, with the proviso that if one of the radicals $R_2$, $R_3$, $R_4$ or $R_5$ is hydroxyl,

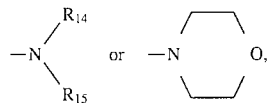

the other radical bonded to the same C atom is other than hydroxyl,

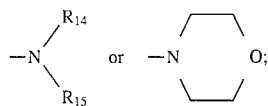

or $R_2$ and $R_3$ or $R_4$ and $R_5$ furthermore, together with the C atom to which they are bonded, form a $C_5$–$C_8$cycloalkylidene ring which is unsubstituted or substituted by $C_1$–$C_4$alkyl, and $R_7$ is hydroxyl, $C_1$–$C_{10}$alkoxy, $C_2$–$C_{12}$ alkoxy interrupted by oxygen;

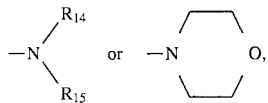

and $R_{14}$ and $R_{15}$ independently of one another are hydrogen, $C_1$–$C_{12}$alkyl, $C_2$–$C_{12}$alkyl which is interrupted by oxygen; $C_5$–$C_9$cycloalkyl or phenyl.

Coating compositions which are likewise preferred are those in which, in formula I, $R_2$, $R_3$, $R_4$ and $R_5$ independently of one another are hydrogen, hydroxyl, $C_1$–$C_{10}$alkoxy,

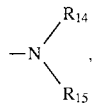

$C_1$–$C_{12}$alkyl, $C_2$–$C_{12}$alkenyl, $C_5$–$C_9$cycloalkyl or $C_5$–$C_9$cycloalkenyl, with the proviso that if one of the radicals $R_2$, $R_3$, $R_4$ or $R_5$ is hydroxyl or

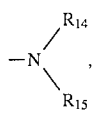

the other radical bonded to the same C atom is other than hydroxyl or

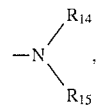

and $R_{14}$ and $R_{15}$ independently of one another are hydrogen or $C_1$–$C_8$alkyl.

Particularly preferred coating compositions are those in which, in formula I, $R_1$ is hydrogen, $C_1$–$C_{12}$alkyl, $C_2$–$C_{12}$alkenyl, $C_4$–$C_{15}$cycloalkyl, $C_{13}$–$C_{26}$polycycloalkyl, benzyl, —$COR_7$, pyrrolidinyl which is unsubstituted or substituted by $C_1$–$C_4$alkyl, $C_1$–$C_4$alkoxy or chlorine; or $R_1$ furthermore is a radical of the formula II or III

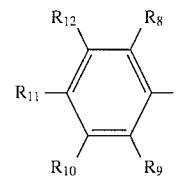

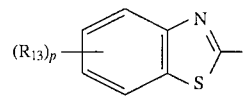

$R_7$ is hydroxyl or $C_1$–$C_{10}$alkoxy, $R_8$, $R_9$, $R_{10}$, $R_{11}$ and $R_{12}$ independently of one another are hydrogen, hydroxyl, chlorine, nitro, —$COR_7$, $C_1$–$C_8$alkyl, $C_1$–$C_4$alkoxy or cyclohexyl; or the radicals $R_9$ and $R_{10}$ or the radicals $R_{10}$ and $R_{11}$ furthermore, together with the carbon atoms to which they are bonded, form a benzo ring, $R_{13}$ is hydrogen, $C_1$–$C_4$alkyl, chlorine or $C_1$–$C_4$alkoxy, $R_{23}$ is hydrogen, $C_1$–$C_8$alkyl or phenyl, $X_1$ is a direct bond, oxygen, sulfur, —$NR_{23}$— or $C_2$–$C_4$alkenylene, with the proviso that if m and n are 0, $X_1$ is other than oxygen and sulfur, and p is 0 or 1.

Coating compositions which are specifically of particular interest are those in which, in formula I, $R_1$ is hydrogen, $C_4$–$C_{15}$cycloalkyl, $C_{13}$–$C_{26}$polycycloalkyl or —$COR_7$; or $R_1$ furthermore is a radical of the formula II or III

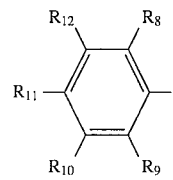

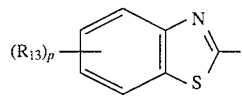

$R_2$, $R_3$, $R_4$ and $R_5$ independently of one another are hydrogen, hydroxyl or —$COR_7$, with the proviso that if one of the radicals $R_2$, $R_3$, $R_4$ or $R_5$ is hydroxyl, the other radical bonded to the same C atom is other than hydroxyl, $R_7$ is hydroxyl, $R_8$ is hydrogen, hydroxyl or —$COR_7$, $R_9$ is hydrogen, $R_{10}$ is hydrogen, $C_1$–$C_4$alkyl or nitro, $R_{11}$ is hydrogen, methyl, nitro or chlorine, or the radicals $R_{10}$ and $R_{11}$, together with the carbon atoms to which they are bonded, form a benzo ring, $R_{12}$ is hydrogen, $C_1$–$C_4$alkyl or —$COR_7$, $R_{23}$ is hydrogen, $X_1$ is a direct bond, oxygen, sulfur, —$NR_{23}$— or vinylene, with the proviso that if m and n are 0, $X_1$ is other than oxygen and sulfur, m is an integer from 0 to 8, n is an integer from 0 to 8, and p is 0.

Coating compositions which are also preferred are those in which, in formula I, $R_1$ is a radical of the formula II

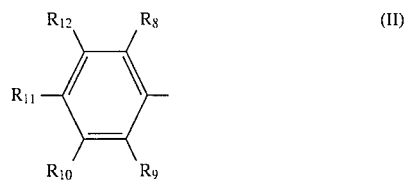

$R_8$, $R_9$, $R_{10}$, $R_{11}$ and $R_{12}$ are hydrogen, $X_1$ is a direct bond, and m and n are 0.

Coating compositions which are also of particular interest are those comprising, as the corrosion inhibitor, at least one titanium or zirconium complex of 2-ethylhexanoic acid, stearic acid, oleic acid, linoleic acid, acetylenecarboxylic acid, cyclohexanecarboxylic acid, naphthenic acid, benzoic acid, naphthoic acid, phenylacetic acid, cinnamic acid, sebacic acid, succinic acid, maleic acid, acetylenedicarboxylic acid, cyclohexanedicarboxylic acid, hydroxynaphthoic acid, hydroxysuccinic acid, anthranilic acid, leucine, phenylalanine, proline, 2-mercaptobenzothiazolylsuccinic acid [®Irgacor 252 (Ciba-Geigy)], 6-[4,6-bis(5-carboxypentylamino)-[1,3,5]-triazin-2-yl-amino]-hexanecarboxylic acid [®Reocor 190 (Ciba-Geigy)], furancarboxylic acid, pyrrolecarboxylic acid, pyrazoledicarboxylic acid, imidazoledicarboxylic acid or nicotinic acid.

Especially preferred coating compositions are those comprising, as the corrosion inhibitor, at least one zirconium complex of benzoic acid, phenylacetic acid, p-methylbenzoic acid, p-chlorobenzoic acid or 2-mercaptobenzothiazolylsuccinic acid.

The titanium or zirconium complexes of compounds of the formula I which are sparingly soluble in water are suitable as corrosion inhibitors in coating compositions for protecting metallic surfaces and also for pretreating metallic substrates. They can be added as such to all liquid or solid organic materials.

The solubility of the titanium and zirconium complexes in water is advantageously <1% by weight, preferably <0.1% by weight, in particular <0.01% by weight.

The titanium or zirconium complexes of compounds of the formula I in coating compositions preferably have the distinctive feature that they are not complexed with any additional volatile uncharged ligands, such as are described, for example, in U.S. Pat. No. 4 243 416 and U.S. Pat. No. 4 243 417, for example amines, alcohols, ethers or mercaptans.

The coating composition is preferably a surface-coating material. An aqueous surface-coating material is specifically preferred.

Surface-coating materials are, for example, lacquers, paints or varnishes. These always comprise an organic film-forming binder, in addition to other optional components.

Preferred organic film-forming binders are epoxy resins, polyurethane resins, polyester resins, acrylic resins and copolymer resins thereof, polyvinyl resins, phenolic resins, alkyd resins or mixtures of such resins.

Suitable organic film-forming binders for the coating composition are all the customary film-forming agents for solvent-containing, but especially for aqueous lacquer compositions. Examples of such film-forming agents are epoxy resins, polyurethane resins, amino resins or mixtures of such resins; a basic aqueous dispersion or a solution of an acid resin.

Organic film-forming binders are of particular interest for aqueous coating compositions, for example alkyd resins; acrylic resins; 2-component epoxy resins; polyurethane resins; polyester resins, which are usually saturated; water-dilutable phenolic resins or dispersions derived therefrom; water-dilutable urea resins; resins based on vinyl/acrylic copolymers; hybrid systems based on, for example, epoxy acrylates.

More specifically, the alkyd resins can be water-dilutable alkyd resin systems which are air-drying or can be employed in the form of stoving systems, if appropriate in combination with water-dilutable melamine resins; they can also be oxidatively drying, air-drying or stoving systems which are used, if appropriate, in combination with aqueous dispersions based on acrylic resins or copolymers thereof with vinyl acetates and the like.

The acrylic resins can be pure acrylic resins, epoxy acrylate hybrid systems, acrylic acid or acrylic acid ester copolymers, combinations with vinyl resins or copolymers with vinyl monomers, such as vinyl acetate, styrene or butadiene. These systems can be air-drying systems or stoving systems.

Water-dilutable epoxy resins in combination with suitable polyamine crosslinking agents have an excellent mechanical and chemical resistance. If liquid epoxy resins are used, addition of organic solvents to aqueous systems can be omitted. The use of solid resins or solid resin dispersions usually requires addition of small amounts of solvent to improve film formation.

Preferred epoxy resins are those based on aromatic polyols, in particular based on bisphenols. The epoxy resins are used in combination with crosslinking agents. The latter can be, in particular, amino- or hydroxy-functional compounds, an acid, an acid anhydride or a Lewis acid. Examples of these are polyamines, polyaminoamides, polymers based on polysulfides, polyphenols, boron fluorides and complex compounds thereof, polycarboxylic acids, 1,2-dicarboxylic acid anhydrides or pyromellitic dianhydride.

Polyurethane resins are derived from polyethers, polyesters and polybutadienes having terminal hydroxyl groups on the one hand and aliphatic or aromatic polyisocyanates on the other hand.

Suitable polyvinyl resins are, for example, polyvinylbutyral, polyvinyl acetate or copolymers thereof.

Suitable phenolic resins are synthetic resins which are built up on phenols as the main component, that is to say, in particular, phenol-, cresol-, xylenol- and resorcinol-formaldehyde resins, alkylphenol resins and condensation products of phenols with acetaldehyde, furfurol, acrolein or other aldehydes. Modified phenolic resins are also of interest. The coating compositions can additionally comprise one or more components from the group consisting of pigments, dyes, fillers, flow control agents, dispersants, thixotropic agents, adhesion promoters, antioxidants, light stabilizers or curing catalysts. They can also additionally comprise other known corrosion inhibitors, for example corrosion-inhibiting pigments, such as phosphate- or borate-containing pigments or metal oxide pigments, or other organic or inorganic corrosion inhibitors, for example salts of nitroisophthalic acid, phosphoric acid esters, technical grade amines or substituted benzotriazoles.

The pigments are, for example, titanium dioxide, iron oxide, aluminium bronze or phthalocyanine blue.

Examples of fillers are talc, aluminium oxide, aluminium silicate, baryte, mica or silicon dioxide. The corrosion inhibitors can also be applied to a carrier. Pulverulent fillers or pigments are particularly suitable for this purpose.

Flow control agents and thixotropic agents are based on, for example, modified bentonites.

Adhesion promoters are based on, for example, modified silanes.

The addition of basic fillers or pigments which have a synergistic effect on the corrosion inhibition in certain binder systems is furthermore of advantage. Examples of such basic fillers and pigments are calcium carbonate or magnesium carbonate, zinc oxide, zinc carbonate, zinc phosphate, magnesium oxide, aluminium oxide, aluminium phosphate or mixtures thereof. Examples of basic organic pigments are those based on aminoanthraquinone.

The corrosion inhibitors can be added to the surface-coating material during preparation thereof, for example during dispersion of these pigments by grinding, or the inhibitor is dissolved in an organic solvent and the solution is then stirred into the coating composition. The solutions of the corrosion inhibitors can also be used for pretreating the metal surface.

In the case of preparation of the organic film-forming binder by polymerization or poly-condensation of monomers, the corrosion inhibitors can already be admixed to the monomers before the polymerization either in the solid form or as a solution.

The titanium and zirconium complexes of compounds of the formula I are advantageously used in an amount of 0.01 to 20% by weight, preferably 0.05 to 5% by weight, in particular 0.1 to 5% by weight, based on the total solids of the coating composition.

The surface-coating material can be applied to the substrate by the customary processes, for example by spraying, dipping, brushing or by electrodeposition. Several layers are often applied. The corrosion inhibitors are primarily added to the basecoat (primer), since they act in particular at the metal-coating boundary. However, they can also additionally be added to the intermediate or topcoat. The coating is cured at room temperature or by heating (stoving) or by irradiation, depending on whether the binder is a physically, heating (stoving) or by irradiation, depending on whether the binder is a physically, chemically or oxidatively drying resin or a thermosetting or radiation-curing resin.

The surface-coating material is preferably an undercoat (primer) for metallic substrates, for example iron, steel, copper, zinc or aluminium, and alloys thereof.

In addition to the anticorrosive action, the titanium and zirconium complexes which are compounds of the formula I have the advantage that they have a favourable influence on the coating-metal adhesion, show no adverse effects on the storage stability of the coating compositions according to the invention, and have a good compatibility with the binder.

The use of the titanium and zirconium complexes of compounds of the formula I as corrosion inhibitors in the coating compositions for metallic surfaces is therefore a preferred embodiment of the present invention.

The present invention also relates to a process for protecting a corrodable metal substrate, which comprises applying to this a coating composition which comprises a) an organic film-forming binder and b) as a corrosion inhibitor, at least one titanium or zirconium complex of a compound of the formula I, and then drying and/or curing the composition.

The invention also relates to novel titanium and zirconium complexes of compounds of the formula I

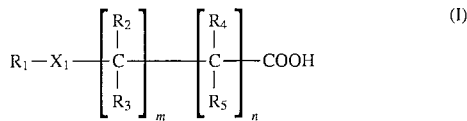

in which $R_1$ is hydrogen, $C_1$–$C_{25}$alkyl, $C_2$–$C_{25}$alkyl which is interrupted by oxygen, sulfur or >N—$R_6$; $C_2$–$C_{24}$alkenyl, $C_4$–$C_{15}$cycloalkyl which is unsubstituted or substituted by $C_1$–$C_4$alkyl; $C_5$–$C_{15}$cycloalkenyl which is unsubstituted or substituted by $C_1$–$C_4$alkyl; $C_{13}$–$C_{26}$polycycloalkyl, $C_7$–$C_9$phenylalkyl which is unsubstituted or substituted on the phenyl ring by $C_1$–$C_4$alkyl; —$COR_7$, a 5- or 6-membered heterocyclic ring which is unsubstituted or substituted by $C_1$–$C_4$alkyl, $C_1$–$C_4$alkoxy, halogen or carboxyl; a benzo-fused 5- or 6-membered heterocyclic ring which is unsubstituted or substituted by $C_1$–$C_4$alkyl, $C_1$–$C_4$alkoxy, halogen or carboxyl; or $R_1$ furthermore is a radical of the formula II, III or IV

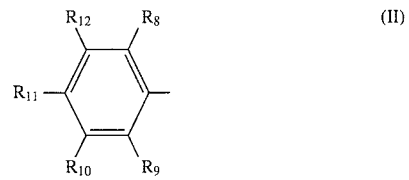

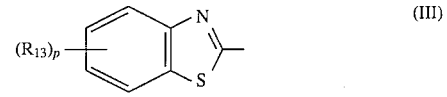

$R_2$, $R_3$, $R_4$ and $R_5$ independently of one another are hydrogen, hydroxyl, $C_1$–$C_{18}$alkoxy, $C_2$–$C_{18}$alkoxy which is interrupted by oxygen, sulfur or >N—$R_6$;

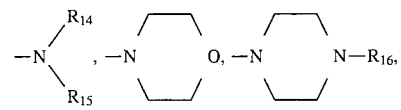

$C_1$–$C_{25}$alkyl, $C_2$–$C_{25}$alkyl which is interrupted by oxygen, sulfur or >N—$R_6$; $C_2$–$C_{24}$alkenyl, $C_5$–$C_{15}$cycloalkyl which is unsubstituted or substituted by $C_1$–$C_4$alkyl; $C_5$–$C_{15}$cycloalkenyl which is unsubstituted or substituted by $C_1$–$C_4$alkyl; phenyl or naphthyl which are unsubstituted or substituted by $C_1$–$C_4$alkyl; $C_7$–$C_9$phenylalkyl which is unsubstituted or substituted on the phenyl ring by $C_1$–$C_4$alkyl; $C_{10}$–$C_{12}$naphthylalkyl which is unsubstituted or substituted on the naphthyl ring by $C_1$–$C_4$alkyl; or —COR$_7$, with the proviso that if one of the radicals R$_2$, R$_3$, R$_4$ or R$_5$ is hydroxyl,

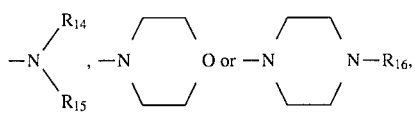

the other radical bonded to the same C atom is other than hydroxyl,

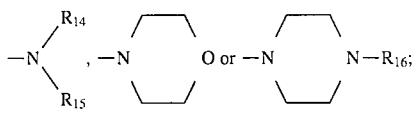

or R$_2$ and R$_3$ or R$_4$ and R$_5$ furthermore, together with the C atom to which they are bonded, form a C$_5$–C$_{12}$cycloalkylidene ring which is unsubstituted or substituted by C$_1$–C$_4$alkyl, R$_6$ is hydrogen or C$_1$–C$_8$alkyl, R$_7$ is hydroxyl, C$_1$–C$_{18}$alkoxy, C$_2$–C$_{18}$alkoxy which is interrupted by oxygen, sulfur or

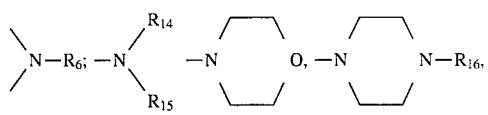

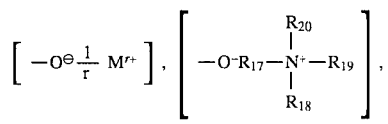

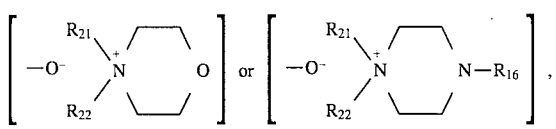

R$_8$, R$_9$, R$_{10}$, R$_{11}$ and R$_{12}$ independently of one another are hydrogen, hydroxyl, halogen, nitro,

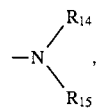

cyano, CF$_3$, —COR$_7$, C$_1$–C$_{25}$alkyl, C$_2$–C$_{25}$alkyl which is interrupted by oxygen, sulfur or >N—R$_6$; C$_1$–C$_{25}$halogenoalkyl, C$_1$–C$_{18}$alkoxy, C$_2$–C$_{18}$alkoxy which is interrupted by oxygen, sulfur or >N—R$_6$; C$_1$–C$_{18}$alkylthio, C$_2$–C$_{24}$alkenyl, C$_5$–C$_{15}$cycloalkyl which is unsubstituted or substituted by C$_1$–C$_4$alkyl; C$_5$–C$_{15}$cycloalkenyl which is unsubstituted or substituted by C$_1$–C$_4$alkyl; phenyl or naphthyl which are unsubstituted or substituted by C$_1$–C$_4$alkyl; C$_7$–C$_9$phenylalkyl which is unsubstituted or substituted on the phenyl ring by C$_1$–C$_4$alkyl; C$_{10}$–C$_{12}$naphthylalkyl which is unsubstituted or substituted on the naphthyl ring by C$_1$–C$_4$alkyl; phenoxy or naphthoxy which are unsubstituted or substituted by C$_1$–C$_4$alkyl; C$_7$–C$_9$-phenylalkoxy which is unsubstituted or substituted on the phenyl ring by C$_1$–C$_4$alkyl; C$_{10}$–C$_{12}$naphthylalkoxy which is unsubstituted or substituted on the naphthyl ring by C$_1$–C$_4$alkyl; or the radicals R$_9$ and R$_{10}$ or the radicals R$_{10}$ and R$_{11}$ or the radicals R$_{11}$ and R$_{12}$ or the radicals R$_8$ and R$_{12}$ furthermore, together with the carbon atoms to which they are bonded, form a benzo ring which is unsubstituted or substituted by C$_1$–C$_4$alkyl, halogen or C$_1$–C$_4$alkoxy, R$_{13}$ is hydrogen, hydroxyl, halogen, nitro, cyano, CF$_3$, C$_1$–C$_{25}$alkyl, C$_2$–C$_{25}$alkyl which is interrupted by oxygen, sulfur or >N—R$_6$; C$_1$–C$_{25}$halogenoalkyl, C$_1$–C$_{18}$alkoxy, C$_2$–C$_{18}$alkoxy which is interrupted by oxygen, sulfur or >N—R$_6$; C$_1$–C$_{18}$alkylthio or C$_2$–C$_{24}$alkenyl;

R$_{14}$ and R$_{15}$ independently of one another are hydrogen, C$_1$–C$_{25}$alkyl, C$_2$–C$_{25}$alkyl which is interrupted by oxygen, sulfur or >N—R$_6$; C$_2$–C$_{24}$alkenyl, C$_5$–C$_{15}$cycloalkyl which is unsubstituted or substituted by C$_1$–C$_4$alkyl; phenyl or naphthyl which are unsubstituted or substituted by C$_1$–C$_4$alkyl, R$_{16}$ is hydrogen or C$_1$–C$_{18}$alkyl, R$_{17}$, R$_{18}$, R$_{19}$, R$_{20}$, R$_{21}$ and R$_{22}$ independently of one another are hydrogen or C$_1$–C$_{25}$alkyl, R$_{23}$ is hydrogen, C$_1$–C$_{25}$alkyl, C$_2$–C$_{25}$alkyl which is interrupted by oxygen, sulfur or >N—R$_6$; C$_2$–C$_{24}$alkenyl, C$_5$–C$_{15}$cycloalkyl which is unsubstituted or substituted by C$_1$–C$_4$alkyl; phenyl or naphthyl which are unsubstituted or substituted by C$_1$–C$_4$alkyl, R$_{24}$ and R$_{25}$ independently of one another are hydrogen, C$_1$–C$_{25}$alkyl, C$_1$–C$_{18}$alkoxy, —X$_2$—(CH$_2$)$_s$COR$_7$ or

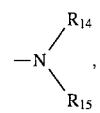

M is an r-valent metal cation,

X$_1$ is a direct bond, oxygen, sulfur, —NR$_{23}$—, C$_1$–C$_{18}$alkylene, C$_2$–C$_{18}$alkylene which is interrupted by oxygen, sulfur or >N—R$_6$, C$_2$–C$_{18}$alkenylene, C$_2$–C$_{18}$alkynylene, C$_2$–C$_{20}$alkylidene, C$_7$–C$_{20}$phenylalkylidene or C$_5$–C$_8$cycloalkylene, with the proviso that if m and n are 0, X$_1$ is other than oxygen and sulfur, X$_2$ is oxygen or —NR$_{23}$—, m and n independently of one another are an integer from 0 to 10, p is an integer from 0 to 4, r is 1,2 or 3, and s is an integer from 1 to 8, and excluding the zirconium complexes of maleic acid, succinic acid, phenylacetic acid, o-phthalic acid, cinnamic acid, benzoic acid, p-nitrobenzoic acid, salicylic acid and mandelic acid.

Preferred groups of the novel titanium and zirconium complexes of compounds of the formula I are as defined as expressly preferred above for the coating compositions.

Titanium and zirconium complexes of the compounds of the formula I which are furthermore preferred are those in which R$_1$ is hydrogen, C$_1$–C$_{18}$alkyl, C$_2$–C$_{18}$alkyl which is interrupted by oxygen, sulfur or >N—R$_6$; C$_2$–C$_{18}$alkenyl, C$_4$–C$_{15}$cycloalkyl which is unsubstituted or substituted by C$_1$–C$_4$alkyl; C$_5$–C$_{12}$cycloalkenyl which is unsubstituted or substituted by C$_1$–C$_4$alkyl; C$_{13}$–C$_{26}$polycycloalkyl, C$_7$–C$_9$phenylalkyl, —COR$_7$, a 5- or 6- membered heterocyclic ring which is unsubstituted or substituted by C$_1$–C$_4$alkyl, C$_1$–C$_4$alkoxy, chlorine or carboxyl; a benzo-fused 5- or 6- membered heterocyclic ring which is unsubstituted for substituted by C$_1$–C$_4$alkyl, C$_1$–C$_4$alkoxy, chlorine or carboxyl; or $R_1$ furthermore is a radical of the formula II, III or IV

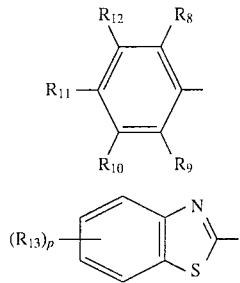 (II)

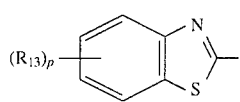 (III)

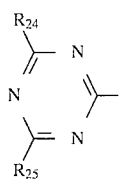 (IV)

$R_2$, $R_3$, $R_4$ and $R_5$ independently of one another are hydrogen, hydroxyl, $C_1$–$C_{12}$alkoxy, $C_2$–$C_{12}$alkoxy which is interrupted by oxygen or sulfur;

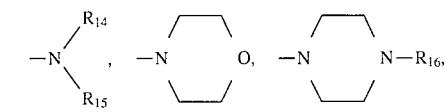

$C_1$–$C_{18}$alkyl, $C_2$–$C_{18}$alkyl which is interrupted by oxygen or sulfur; $C_2$–$C_{18}$alkenyl, $C_5$–$C_{15}$cycloalkyl, $C_5$–$C_{15}$cycloalkenyl, phenyl, naphthyl, $C_7$–$C_9$phenylalkyl, $C_{10}$–$C_{12}$naphthylalkyl or —$COR_7$, with the proviso that if one of the radicals $R_2$, $R_3$, $R_4$ or $R_5$ is hydroxyl,

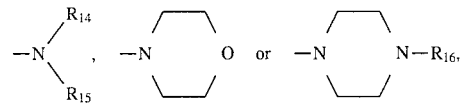

the other radical bonded to the same C atom is other than hydroxyl,

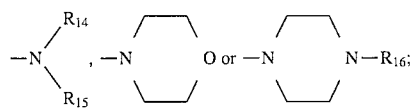

or $R_2$ and $R_3$ or $R_4$ and $R_5$ furthermore, together with the C atom to which they are bonded, form a $C_5$–$C_8$cycloalkylidene ring which is unsubstituted or substituted by $C_1$–$C_4$alkyl, $R_7$ is hydroxyl, $C_1$–$C_{12}$alkoxy, $C_2$–$C_{12}$alkoxy which is interrupted by oxygen or sulfur;

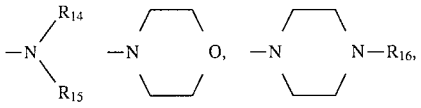

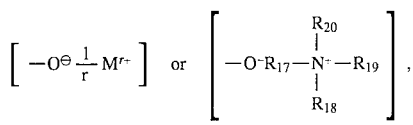

$R_8$, $R_9$, $R_{10}$, $R_{11}$ and $R_{12}$ independently of one another are hydrogen, hydroxyl, halogen, nitro, cyano, $CF_3$, —$COR_7$, $C_1$–$C_{18}$alkyl, $C_2$–$C_{18}$alkyl which is interrupted by oxygen or sulfur; $C_1$–$C_{18}$halogenoalkyl, $C_1$–$C_{12}$alkoxy, $C_2$–$C_{12}$alkoxy which is interrupted by oxygen or sulfur; $C_1$–$C_{12}$alkylthio, $C_2$–$C_{18}$alkenyl, $C_5$–$C_{12}$cycloalkyl, $C_5$–$C_{12}$cycloalkenyl, phenyl, naphthyl, $C_7$–$C_9$-phenylalkyl, $C_{10}$–$C_{12}$naphthylalkyl, phenoxy, naphthoxy, $C_7$–$C_9$phenylalkoxy or $C_{10}$–$C_{12}$naphthylalkoxy; or the radicals $R_9$ and $R_{10}$ or the radicals $R_{10}$ and $R_{11}$ or the radicals $R_{11}$ and $R_{12}$ or the radicals $R_8$ and $R_{12}$ furthermore, together with the carbon atoms to which they are bonded, form a benzo ring which is unsubstituted or substituted by $C_1$–$C_4$alkyl or chlorine, $R_{13}$ is hydrogen, hydroxyl, halogen, nitro, cyano, $CF_3$, $C_1$–$C_{18}$alkyl, $C_2$–$C_{18}$alkyl which is interrupted by oxygen or sulfur; $C_1$–$C_{18}$halogenoalkyl, $C_1$–$C_{12}$alkoxy, $C_2$–$C_{12}$alkoxy which is interrupted by oxygen or sulfur; $C_1$–$C_{12}$alkylthio or $C_2$–$C_{18}$alkenyl, $R_{14}$ and $R_{15}$ independently of one another are hydrogen, $C_1$–$C_{18}$alkyl, $C_2$–$C_{18}$alkyl which is interrupted by oxygen or sulfur; $C_2$–$C_{18}$alkenyl, $C_5$–$C_{12}$cycloalkyl, phenyl or naphthyl, $R_{16}$ is hydrogen or $C_1$–$C_{12}$alkyl, $R_{17}$, $R_{18}$, $R_{19}$, $R_{20}$, $R_{21}$ and $R_{22}$ independently of one another are hydrogen or $C_1$–$C_{18}$alkyl, $R_{23}$ is hydrogen, $C_1$–$C_{18}$alkyl, $C_2$–$C_{18}$alkyl which is interrupted by oxygen or sulfur; $C_2$–$C_{18}$alkenyl, $C_5$–$C_{12}$cycloalkyl, phenyl or naphthyl, $R_{24}$ and $R_{25}$ independently of one another are hydrogen, $C_1$–$C_{18}$alkyl, $C_1$–$C_{12}$alkoxy, —$X_2$—$(CH_2)_sCOR_7$ or

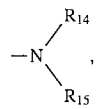

$X_1$ is a direct bond, oxygen, sulfur, —$NR_{23}$—, $C_1$–$C_{12}$alkylene, $C_2$–$C_{12}$alkylene which is interrupted by oxygen or sulfur; $C_2$–$C_{12}$alkenylene, $C_2$–$C_{12}$alkynylene, $C_2$–$C_{16}$alkylidene, $C_7$–$C_{16}$phenylalkylidene or $C_5$–$C_8$cycloalkylene, with the proviso that if m and n are 0, $X_1$ is other than oxygen and sulfur, $X_2$ is —$NR_{23}$—, p is 0, 1 or 2, and s is an integer from 2 to 7.

Titanium and zirconium complexes of compounds of the formula I which are also preferred are those in which $R_1$ is hydrogen, $C_1$–$C_{12}$alkyl, $C_3$–$C_{12}$alkyl which is interrupted by oxygen; $C_2$–$C_{12}$alkenyl, $C_4$–$C_{15}$cycloalkyl, $C_5$–$C_8$cycloalkenyl, $C_{13}$–$C_{26}$polycycloalkyl, benzyl, —$COR_7$, or thienyl, tetrahydrofuranyl, furyl, pyrrolidinyl, pyrrolyl, thiazolyl, isothiazolyl, triazolyl, tetrazolyl, oxazolyl, isoxazolyl, pyridyl, piperidinyl, pyrazinyl, piperazinyl or triazinyl which are unsubstituted or substituted by $C_1$–$C_4$alkyl, $C_1$–$C_4$alkoxy, chlorine or carboxyl or benzo-fused; or $R_1$ furthermore is a radical of the formula II, III or IV

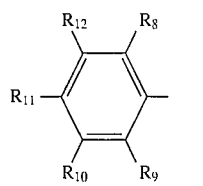 (II)

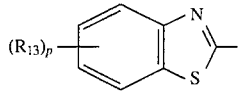 (III)

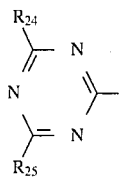 (IV)

$R_7$ is hydroxyl, $C_1$–$C_{10}$-alkoxy, $C_2$–$C_{12}$alkoxy which is interrupted by oxygen;

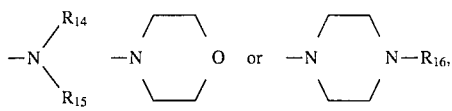

$R_8$, $R^9$, $R^{10}$, $R^{11}$ and $R^{12}$ independently of one another are hydrogen, hydroxyl, chlorine, nitro,

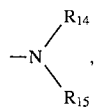

—$COR_7$, $C_1$–$C_{12}$alkyl, $C_2$–$C_{16}$alkyl which is interrupted by oxygen; $C_1$–$C_{12}$halogenoalkyl, $C_1$–$C_{12}$alkoxy, $C_2$–$C_{12}$alkoxy which is interrupted by oxygen; $C_2$–$C_{12}$alkenyl, $C_5$–$C_9$cycloalkyl, $C_5$–$C_9$cycloalkenyl, phenyl, naphthyl, $C_7$–$C_9$phenylalkyl, $C_{10}$–$C_{12}$naphthylalkyl, phenoxy or $C_7$–$C_9$phenylalkoxy; or the radicals $R_9$ and $R_{10}$ or the radicals $R_{10}$ and $R_{11}$ furthermore, together with the carbon atoms to which they are bonded, form a benzo ring, $R_{13}$ is hydrogen, hydroxyl, chlorine, nitro, $C_1$–$C_{12}$alkyl, $C_2$–$C_{12}$alkyl which is interrupted by oxygen; $C_1$–$C_{10}$alkoxy or $C_2$–$C_{10}$alkoxy which is interrupted by oxygen, $R_{14}$ and $R_{15}$ independently of one another are hydrogen, $C_1$–$C_{12}$alkyl, $C_2$–$C_{12}$alkyl which is interrupted by oxygen; $C_5$–$C_9$cycloalkyl or phenyl, $R_{16}$ is hydrogen or $C_1$–$C_8$alkyl, $R_{23}$ is hydrogen, $C_1$–$C_{12}$alkyl, $C_3$–$C_{12}$alkyl which is interrupted by oxygen; $C_2$–$C_{12}$alkenyl, $C_5$–$C_9$cycloalkyl or phenyl, $R_{24}$ and $R_{25}$ independently of one another are hydrogen or —$X_2$—$(CH_2)_sCOR_7$ or

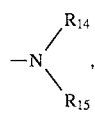

$X_1$ is a direct bond, oxygen, sulfur, —$NR_{23}$—, $C_1$–$C_8$alkylene, $C_2$–$C_8$alkenylene, $C_2$–$C_8$alkenylene, $C_2$–$C_8$—alkynylene, $C_2$–$C_{12}$alkylidene, $C_7$–$C_{12}$phenylalkylidene or $C_5$–$C_8$cycloalkylene, with the proviso that if m and n are 0, $X_1$ is other than oxygen and sulfur, $X_2$ is —$NR_{23}$—, p is 0 or 1, and s is an integer from 3 to 6.

Titanium and zirconium complexes of compounds of the formula I which are likewise preferred are those in which $R_2$, $R_3$, $R_4$ and $R_5$ independently of one another are hydrogen, hydroxyl, $C_1$–$C_{10}$alkoxy, $C_2$–$C_{12}$alkoxy which is interrupted by oxygen;

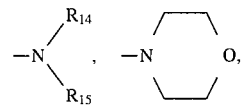

$C_1$–$C_{12}$alkyl, $C_2$–$C_{18}$alkyl which is interrupted by oxygen; $C_2$–$C_{12}$alkenyl, $C_5$–$C_9$cycloalkyl, $C_5$–$C_9$cycloalkenyl, phenyl, naphthyl, $C_7$–$C_9$phenylalkyl or —$COR_7$, with the proviso that if one of the radicals $R_2$, $R_3$, $R_4$ or $R_5$ is hydroxyl,

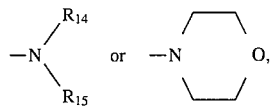

the other radical bonded to the same C atom is other than hydroxyl,

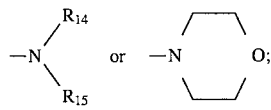

or $R_2$ and $R_3$ or $R_4$ and $R_5$ furthermore, together with the C atom to which they are bonded, form a $C_5$–$C_8$cycloalkylidene ring which is unsubstituted or substituted by $C_1$–$C_4$alkyl, and $R_7$ is hydroxyl, $C_1$–$C_{10}$alkoxy, $C_2$–$C_{12}$alkoxy interrupted by oxygen;

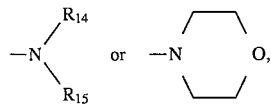

and $R_{14}$ and $R_{15}$ independently of one another are hydrogen, $C_1$–$C_{12}$alkyl, $C_2$–$C_{12}$alkyl which is interrupted by oxygen; $C_5$–$C_9$cycloalkyl or phenyl.

Titanium and zirconium complexes of compounds of the formula I which are particularly preferred are those in which $R_2$, $R_3$, $R_4$ and $R_5$ independently of one another are hydrogen, hydroxyl, $C_1$–$C_{10}$alkoxy,

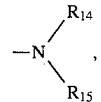

$C_1$–$C_{12}$alkyl, $C_2$–$C_{12}$alkenyl, $C_5$–$C_9$cycloalkyl or $C_5$–$C_9$cycloalkenyl, with the proviso that if one of the radicals $R_2$, $R_3$, $R_4$ or $R_5$ is hydroxyl or

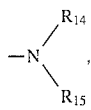

the other radical bonded to the same C atom is other than hydroxyl or

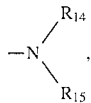

and $R_{14}$ and $R_{15}$ independently of one another are hydrogen or $C_1$–$C_8$alkyl.

Titanium and zirconium complexes of compounds of the formula I which are of particular interest are those in which $R_1$ is hydrogen, $C_1$–$C_{12}$alkyl, $C_2$–$C_{12}$alkenyl, $C_4$–$C_{15}$cycloalkyl, $C_{13}$–$C_{26}$polycycloalkyl, benzyl, —$COR_7$, pyrrolidinyl which is unsubstituted or substituted by $C_1$–$C_4$alkyl, $C_1$–$C_4$alkoxy or chlorine; or $R_1$ furthermore is a radical of the formula II or III

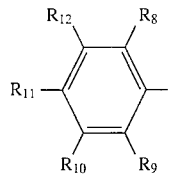

$R_7$ is hydroxyl or $C_1$–$C_{10}$alkoxy, $R_8$, $R_9$, $R_{10}$, $R_{11}$ and $R_{12}$ independently of one another are hydrogen, hydroxyl, chlorine, nitro, —$COR_7$, $C_1$–$C_8$alkyl, $C_1$–$C_4$alkoxy or cyclohexyl; or the radicals $R_9$ and $R_{10}$ or the radicals $R_{10}$ and $R_{11}$ furthermore, together with the carbon atoms to which they are bonded, form a benzo ring, $R_{13}$ is hydrogen, $C_1$–$C_4$alkyl, chlorine or $C_1$–$C_4$alkoxy, $R_{23}$ is hydrogen, $C_1$–$C_8$alkyl or phenyl, $X_1$ is a direct bond, oxygen, sulfur, —$NR_{23}$— or $C_2$–$C_4$alkenylene, with the proviso that if m and n are 0, $X_1$ is other than oxygen and sulfur, and p is 0 or 1.

Titanium and zirconium complexes of compounds of the formula I which are specifically of particular interest are those in which $R_1$ is hydrogen, $C_4$–$C_{15}$cycloalkyl, $C_{13}$–$C_{26}$polycycloalkyl or —$COR_7$; or $R_1$ furthermore is a radical of the formula II or III

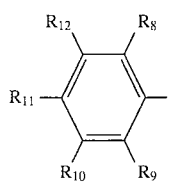

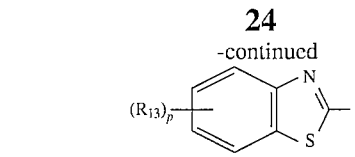

$R_2$, $R_3$, $R_4$ and $R_5$ independently of one another are hydrogen, hydroxyl or —$COR_7$, with the proviso that if one of the radicals $R_2$, $R_3$, $R_4$ or $R_5$ is hydroxyl, the other radical bonded to the same C atom is other than hydroxyl, $R_7$ is hydroxyl, $R_8$ is hydrogen, hydroxyl or —$COR_7$, $R_9$ is hydrogen, $R_{10}$ is hydrogen, $C_1$–$C_4$alkyl or nitro, $R_{11}$ is hydrogen, methyl, nitro or chlorine, or the radicals $R_{10}$ and $R_{11}$, together with the carbon atoms to which they are bonded, form a benzo ring, $R_{12}$ is hydrogen, $C_1$–$C_4$alkyl or —$COR_7$, $R_{23}$ is hydrogen, $X_1$ is a direct bond, oxygen, sulfur, —$NR_{23}$— or vinylene, with the proviso that if m and n are 0, $X_1$ is other than oxygen and sulfur, m is an integer from 0 to 8, n is an integer from 0 to 8, and p is 0.

The titanium and zirconium complexes of compounds of the formula I can be prepared in a manner known per se.

The invention also relates to a coating composition comprising a) an organic film-forming binder and b) as a corrosion inhibitor, at least one titanium or zirconium complex obtainable by reaction of a carboxylic acid of the formula I or an alkali metal salt thereof, in which the general symbols are as defined, with a titanium or zirconium compound.

The titanium or zirconium compound employed is advantageously an organic titanium or zirconium compound or an inorganic titanium or zirconium compound.

Examples of organic titanium and zirconium compounds are, in particular, alcoholates, for example zirconium n-propoxide, zirconium isopropoxide, zirconium n-butoxide, titanium n-propoxide, titanium iso-propoxide, titanium ethoxide or titanium n-butoxide; or carboxylates, such as, for example, acetates, in particular zirconium acetate.

Examples of inorganic titanium and zirconium compounds are halides, in particular chlorides, nitrates, carbonates, hydroxides and sulfates. Zirconium carbonate, zirconium sulfate, zirconium oxychloride, zirconium hydroxide and titanium oxychloride are of particular interest.

In the preparation of titanium or zirconium complexes starting from compounds of the formula I and inorganic titanium and zirconium compounds, for example zirconium carbonate, the reaction is preferably carried out in water at elevated temperature, in particular temperatures of 50° to 100° C.

The reaction also takes place in a mixture of an organic solvent with water. Particularly preferred mixtures are those of water with aromatic hydrocarbons, for example toluene or xylene; or alcohols, for example methanol, ethanol, n-propanol, isopropanol, n-butanol or 2-butanol. Toluene and 2-butanol are particularly preferred. The water/organic solvent ratio can be varied as desired. A solvent ratio of, for example, water/toluene or water/2-butanol (volume/volume) of 1:10 to 10:1, in particular 1:5 to 5:1, for example 1:2 to 2:1, is preferred.

If organic titanium or zirconium compounds, for example titanium n-propoxide or zirconium n-propoxide, are used, the reaction is preferably carried out in an anhydrous organic solvent. Suitable organic solvents are all those which are chemically inert to bases under the reaction conditions. The preferred solvents are aromatic hydrocarbons, for example toluene or xylene; aliphatic hydrocarbons, for example pentane, hexane, heptane or octane and isomer mixtures thereof; halogenated hydrocarbons, for example methylene chloride or chloroform or 1,2-dichloroethane; ethers, for example diethyl ether, dibutyl ether, 1,4-dioxane or tetrahydrofuran; and furthermore acetonitrile, dimethylformamide, dimethyl sulfoxide or N-methylpyrrolidone.

In the preparation of titanium and zirconium complexes starting from compounds of the formula I and organic titanium and zirconium compounds, the reaction is preferably carried out in toluene at elevated temperature, in particular at temperatures of 30° to 80° C.

The hydrolysis of the titanium and zirconium complexes of compounds of the formula I prepared from the organic titanium or zirconium compounds and the carboxylic acids of the formula I is advantageously carried out in the form of a suspension in water. The products are preferably isolated by filtration of the reaction mixture and subsequent drying of the residue under a high vacuum at room temperature.

The reaction of alkali metal salts of carboxylic acids of the formula I, in particular sodium carboxylates, with inorganic titanium or zirconium compounds, for example zirconium sulfate, to give the titanium and zirconium complexes of compounds of the formula I is preferably carried out in a solvent, for example water or a mixture of water and an organic solvent, at room temperature. The products are preferably isolated by filtration of the reaction mixture and subsequent drying of the residue under a high vacuum at room temperature.

The alkali metal salts of carboxylic acids of the formula I can also be prepared in situ from the corresponding carboxylic acid of the formula I with one equivalent of dilute alkali metal hydroxide solution.

The carboxylic acids of the formula I can be used in excess, an equimolar amount or less than the equimolar amount with respect to the titanium or zirconium compound employed. The molar ratio of carboxylic acid of the formula I to the titanium or zirconium compound can be 20:1 to 1:10. A ratio of 10:1 to 1:3 is preferred.

The present invention therefore also relates to a coating composition comprising a) an organic film-forming binder and b) as a corrosion inhibitor, at least one titanium or zirconium complex obtainable by reaction of a carboxylic acid of the formula I or an alkali metal salt thereof, in which the general symbols are as defined, with a titanium or zirconium compound, wherein the molar ratio of the carboxylic acid of the formula I to the titanium or zirconium compound is 20:1 to 1:10, in particular 10:1 to 1:5, for example 5:1 to 1:5.

The titanium and zirconium complexes of compounds of the formula I can also be still complexed with free acid (formula I), water or with other anions, such as hydroxides, which are present in the reaction medium. In the case of titanium or zirconium acetates or titanium or zirconium alkoxides, the titanium and zirconium complexes of compounds of the formula I can contain acetate or alkoxide anions.

On the basis of the above statements, the percentage metal weight content in the titanium and zirconium complexes of the carboxylic acids of the formula I can vary. Preferred complexes have a metal content of 5 to 50% by weight, preferably 5 to 45% by weight, for example 5 to 40% by weight.

The structures of the titanium and zirconium complexes of carboxylic acids of the formula I can vary according to the preparation method and the molar ratios of the carboxylic acids of the formula I and titanium or zirconium compound employed.

The present invention therefore also relates to products obtainable by reaction of a carboxylic acid of the formula I or an alkali metal salt thereof with a titanium or zirconium compound.

The carboxylic acids of the formula I are known in the literature and their preparation is described in the above-mentioned literature references. Many carboxylic acids of the formula I are commercially obtainable. The preparation of some particularly preferred carboxylic acids of the formula I which are used in the following examples is described, for example, in U.S. Pat. No. 4,612,378, GB-A-1,295,432 or J. Chem. Soc., Perkin Trans. I, 7, 932–935 (1972).

The following examples illustrate the invention in more detail. Parts and percentages are by weight.

EXAMPLE 1

Preparation of the zirconium complex of 4-methylbenzoic acid with basic zirconium carbonate (compound (101)).

A suspension of 34.27 g (0.25 mol) of 4-methylbenzoic acid and 50 g (0.18 mol) of basic zirconium carbonate (zirconium content 32.88%) in 500 ml of water is heated slowly to 90° C., while stirring intensively. Stirring of the reaction mixture is then continued at 90° C. for a further 45 minutes. The water is decanted off hot and the residue is extracted with ethyl acetate. The organic phases are combined and concentrated on a vacuum rotary evaporator. After the residue has been dried under a high vacuum at 25° C., 48.4 g of the zirconium complex of 4-methylbenzoic acid (compound (101)) result as a white powder. Analysis found: Zr 28.1%; C 41.8%; H 3.85%; $H_2O$ 1.5%.

EXAMPLE 2

Preparation of the zirconium complex of 4-methylbenzoic acid with zirconium(IV) n-propoxide (compound (102)).

A solution of 20.42 g (0.15 mol) of 4-methylbenzoic acid and 66.52 g (0.15 mol) of zirconium(IV) n-propoxide (Fluka, zirconium content 20%) in 200 ml of dry toluene is stirred at 50° C. under a nitrogen atmosphere for 18 hours. The reaction mixture is then cooled and concentrated on a vacuum rotary evaporator. After the residue has been dried under a high vacuum at 25° C., 63.7 g of the zirconium complex of 4-methylbenzoic acid (compound (102) result as an orange oil. Analysis found: Zr 21.24%; C 51.42%; H 7.17%.

EXAMPLE 3

Preparation of the zirconium complex of 4-methylbenzoic acid with zirconium(IV) n-propoxide and subsequent hydrolysis (compound (103)).

A solution of 38.5 g (95 mmol) of the zirconium complex of 4-methylbenzoic acid, prepared from 4-methylbenzoic acid and zirconium(IV) n-propoxide (Example 2, compound (102)), in 10 ml of acetone is introduced into 1 liter of water and the mixture is stirred at room temperature for 30 minutes. The reaction mixture is filtered and the residue is extracted with a little methylene chloride. The residue is dried under a high vacuum at room temperature. 21.15 g of the zirconium complex of 4-methylbenzoic acid (compound (103)) result as a beige powder. Analysis found: Zr 33.78%; C 36.01%; H 3.89%.

EXAMPLE 4

Preparation of the titanium complex of 4-methylbenzoic acid with titanium iso-propoxide (compound (104)).

59.08 g of the titanium complex of 4-methylbenzoic acid (compound (104)) are obtained as a yellow powder analogously to Example 2 from 23.15 g (0.17 mol) of 4-methylbenzoic acid and 43.33 g (0.17 mol of titanium(IV) iso-propoxide (Fluka, titanium content 16.9%) in 200 ml of dry toluene. Analysis found: Ti 13.43%; C 46.76%; H 5.79%.

EXAMPLE 5

Preparation of the titanium complex of 4-methylbenzoic acid with titanium iso-propoxide and subsequent hydrolysis (compound (105))

37.3 g (0.103 mol) of the titanium complex of 4-methylbenzoic acid, prepared from 4-methylbenzoic acid with titanium iso-propoxide (Example 4, compound (104)), are suspended in 1 liter of water and the suspension is stirred at room temperature for 3 hours. After filtration, the residue on the filter is extracted with a little methylene chloride and the residue which remains is dried under a high vacuum at room temperature. 13.47 g of the titanium complex of 4-methylbenzoic acid (compound (105)) result as a yellow powder. Analysis found: Ti 23.2%; C 43.08%; H 4.41%.

EXAMPLE 6

Preparation of the zirconium complex of 4-methylbenzoic acid with zirconium n-propoxide (compound (106)).

63.6 g of the zirconium complex of 4-methylbenzoic acid (compound (106)) are obtained as a beige powder analogously to Example 2 from 35.4 g (0.26 mol) of 4-methylbenzoic acid and 57.65 g (0.13 mol) of zirconium(IV) n-propoxide (Fluka, zirconium content 20%) in 200 ml of dry toluene. Analysis found: Zr 18.69%; C 50.6%; H 5.23%.

EXAMPLE 7

Preparation of the zirconium complex of 4-methylbenzoic acid with zirconium n-propoxide and subsequent hydrolysis (compound (107)).

40.74 g (85 mmol) of the zirconium complex of 4-methylbenzoic acid prepared from 4-methylbenzoic acid with zirconium(IV) n-propoxide (Example 6, compound (106)), are suspended in 1 liter of water and the suspension is stirred at room temperature for 3 hours. After filtration, the residue is dried under a high vacuum at room temperature. 29.55 g of the zirconium complex of 4-methylbenzoic acid (compound (107)) results as a white powder. Analysis found: Zr 21.67%; C 51.43%; H 4.8%.

EXAMPLE 8

Preparation of the titanium complex of 4-methylbenzoic acid with titanium iso-propoxide (compound (108)).

62 g of the titanium complex of 4-methylbenzoic acid (compound (108)) are obtained as a yellow oil analogously to Example 2 from 38.12 g (0.28 mol) of 4-methylbenzoic acid and 39.8 g (0.14 mol) of titanium(IV) iso-propoxide (Fluka, titanium content 16.9%) in 200 ml of dry toluene. Analysis found: Ti 10.86%; C 59.45%; H 6.1%.

EXAMPLE 9

Preparation of the titanium complex of 4-methylbenzoic acid with titanium iso-propoxide and subsequent hydrolysis (compound (109)).

39.01 g (89 mmol) of the titanium complex of 4-methylbenzoic acid, prepared from 4-methylbenzoic acid with titanium iso-propoxide (Example 8, compound (108)), are suspended in 1 l of water and the suspension is stirred at room temperature for 3 hours. After filtration, the residue is dried under a high vacuum at room temperature. 25.27 g of the titanium complex of 4-methylbenzoic acid (compound (109)) result as a white powder. Analysis found: Ti 12.55%; C 58.06%; 5.43%.

EXAMPLE 10

Preparation of the zirconium complex of 3-(4-hydroxyphenyl)propionic acid with zirconium n-propoxide (compound (110)).

8.31 g (50 mmol) of 3-(4-hydroxyphenyl)propionic acid are added to a solution of 22.67 g (50 mmol) of zirconium(IV) n-propoxide (Fluke, zirconium content 20%) in 100 ml of dry 1,4-dioxane and the mixture is stirred at 50° C. for 24 hours. The suspension is then filtered and the residue is dried under a high vacuum at room temperature. 12.78 g of the zirconium complex of 3-(4-hydroxyphenyl)propionic acid (compound (110)) result as a white powder. Analysis found: Zr 28.92%; C 39.87%; H 4.72%.

EXAMPLE 11

Preparation of the zirconium complex of 3-(4-hydroxyphenyl)propionic acid with zirconium carbonate (compound (111)).

11.7 g of the zirconium complex of 3-(4-hydroxyphenyl)propionic acid (compound (111)) are obtained as a white powder analogously to Example 1 from 10.92 g (65 mmol) of 3-(4-hydroxyphenyl)propionic acid and 12.5 g (45 mmol) of basic zirconium carbonate (zirconium content 32.88%) in 125 ml of water. Analysis found: Zr 32.05%; C 34.55%; H 3.73%; $H_2O$ 3.3%.

EXAMPLE 12

Preparation of the zirconium complex of benzothiazole-2-thioylsuccinic acid with zirconium n-propoxide (compound (112)).

11.94 g of the zirconium complex of benzothiazole-2-thioylsuccinic acid (compound (112)) are obtained as a yellow powder analogously to Example 2 from 7.28 g (26 mmol) of benzothiazole-2-thioylsuccinic acid [US-A-4 612 378] and 11.33 g (25 mmol) of zirconium(IV) n-propoxide (Fluka, zirconium content 20%) in 100 ml of dry toluene. Analysis found: Zr 19.17%; C 40.36%; H 4.34%; N 2.49%; S 12.68%.

EXAMPLE 13

Preparation of the zirconium complex of benzothiazole-2-thioylsuccinic acid with zirconium n-propoxide (compound (113)).

20.36 g of the zirconium complex of benzothiazole-2-thioylsuccinic acid (compound (113)) are obtained as a beige powder analogously to Example 2 from 7.28 g (26 mmol) of benzothiazole-2-thioylsuccinic acid [US-A-4 612 378] and 22.67 g (50 mmol) of zirconium(IV) n-propoxide (Fluka,

EXAMPLE 14

Preparation of the zirconium complex of 3-(3,5-di-tert-butyl-4-hydroxyphenyl)propionic acid with zirconium n-propoxide (compound (114)).

22.7 g of the zirconium complex of 3-(3,5-di-tert-butyl-4-hydroxyphenyl)propionic acid (compound (114)) are obtained as a yellow oil analogously to Example 2 from 11.14 g (40 mmol) of 3-(3,5-di-tert-butyl-4-hydroxyphenyl)propionic acid [GB-A-1 295 432, Example 1] and 18.14 g (40 mmol) of zirconium(IV) n-propoxide (Fluka, zirconium content 20%) in 80 ml of dry toluene. Analysis found: Zr 16.49%; C 57.11%; H 8.27%.

EXAMPLE 15

Preparation of the zirconium complex of 4-(4-methylphenyl)butyric acid with zirconium n-propoxide (compound (115)).

11.2 g of the zirconium complex of 4-(4-methylphenyl)butyric acid (compound (115)) are obtained as an orange oil analogously to Example 2 from 4.56 g (25 mmol) of 4-(4-methylphenyl)butyric acid and 11.33 g (25 mmol) of zirconium(IV) n-propoxide (Fluka, zirconium content 20%) in 50 ml of dry toluene. Analysis found: Zr 21.13%; C 53.21%; H 7.33%.

EXAMPLE 16

Preparation of the zirconium complex of 3-(4-methylphenylthio)propionic acid with zirconium n-propoxide (compound (116)).

7.03 g of the zirconium complex of 3-(4-methylphenylthio)propionic acid (compound (116)) are obtained as an orange oil analogously to Example 2 from 2.94 g (15 mmol) of 3-(4-methylphenylthio)propionic acid and 6.8 g (15 mmol) of zirconium(IV) n-propoxide (Fluka, zirconium content 20%) in 50 ml of dry toluene. Analysis found: Zr 20.39%; C 48.37%; H 6.84%; S 6.85%.

EXAMPLE 17

Preparation of the zirconium complex of 3-(4-methylphenoxy)propionic acid with zirconium carbonate (compound (117)).

4.56 g of the zirconium complex of 3-(4-methylphenoxy)propionic acid (compound (117)) are obtained as a beige powder analogously to Example 1 from 4.97 g (27.6 mmol) of 3-(4-methylphenoxy)propionic acid and 5.3 g (19 mmol) of basic zirconium carbonate (zirkonium content 32.88%) in 53 ml of water. Analysis found: Zr 22.45%; C 44.78%; H 4.97%; $H_2O$ 0.85%.

EXAMPLE 18

Preparation of the zirconium complex of 3-(4-methylphenoxy)propionic acid with zirconium carbonate (compound (118)).

A suspension of 4.97 g (27.6 mmol) of 3-(4-methylphenoxy)propionic acid and 5.3 g (19.1 mmol) of basic zirconium carbonate (zirconium content 32.88%) in 53 ml of water and 53 ml of toluene is heated to 85° C., while stirring intensively. Stirring of the reaction mixture is then continued at 85° C. for a further 45 minutes. The still hot organic phase is separated off and concentrated on a vacuum rotary evaporator. The residue is dried under a high vacuum at room temperature. 5.53 g of the zirconium complex of 3-(4-methylphenoxy)propionic acid (compound (118)) result as a brown powder. Analysis found: Zr 25.07%; C 43.21%; H 5.08%; $H_2O$ 1.09%.

EXAMPLE 19

Preparation of the zirconium complex of 3-(4-methylphenoxy)propionic acid with zirconium sulfate (compound (119)).

A solution of 2.23 g (6 mmol) of zirconium sulfate [$Zr(SO_4)_2$·4 $H_2O$, supplier: Alfa] in 4.2 ml of water is added to a solution of 4.87 g (27 mmol) of 3-(4-methylphenoxy)propionic acid in 27 ml 1N sodium hydroxide solution. The precipitate is filtered off, washed with water and dried under a high vacuum at room temperature. 3.09 g of the zirconium complex of 3-(4-methylphenoxy)propionic acid (compound (119)) result as a beige powder. Analysis found: Zr 13.73%; C 52.65%; H 5.49; $H_2O$ 1.58%; $SO_4^{2-}$ 0,25%.

EXAMPLE 20

Preparation of the zirconium complex of 3-(4-methylphenoxy)propionic acid with zirconium n-propoxide (compound (120)).

6.57 g of the zirconium complex of 3-(4-methylphenoxy)propionic acid (compound (120)) are obtained as a brown oil analogously to Example 2 from 3.06 g (17 mmol) of 3-(4-methylphenoxy)propionic acid and 7.71 g (17 mmol) of zirconium(IV) n-propoxide (Fluka, zirkonium content 20%) in 50 ml of dry toluene. Analysis found: Zr 23.59%; C 47.82%; H 7.43%.

EXAMPLE 21

Preparation of the zirconium complex of 3-(4-methylphenylamino)propionic acid with zirconium carbonate (compound (121)).

2.3 g of the zirconium complex of 3-(4-methylphenylamino)propionic acid (compound (121)) are obtained as an orange powder analogously to Example 1 from 4.2 g (23.4 mmol) of 3-(4-methylphenylamino)propionic acid [J. Chem. Soc., Perkin Trans. I, 7, 932–935 (1972)] and 4.5 g (16.2 mmol) of basic zirconium carbonate (zirconium content 32.88%) in 45 ml of water. Analysis found: Zr 22.65%; C 45.13%; H 5.32%; N 4.84%; $H_2O$ 0.68%.

EXAMPLE 22

Preparation of the zirconium complex of 3-(4-methylphenylamino)propionic acid with zirconium carbonate (compound (122)).

3.18 g of the zirconium complex of 3-(4-methylphenylamino)propionic acid (compound (122)) are obtained as an orange powder analogously to Example 18 from 3.73 g (20.8 mmol) of 3-(4-methylphenylamino)propionic acid with 4.0 g (14.4 mmol) of basic zirconium carbonate (zirconium content 32.88%) in 40 ml of water and 40 ml of toluene. Analysis found: Zr 18.94%; C 49.34%; H 5.86%; N 4.78%; $H_2O$ 1.15%.

EXAMPLE 23

Preparation of the zirconium complex of 3-(4-methylphenylamino)propionic acid with zirconium n-propoxide (compound (123)).

4.53 g of the zirconium complex of 3-(4-methylphenylamino)propionic acid (compound (123)) are obtained as a yellow oil analogously to Example 2 from 1.61 g (9 mmol) of 3-(4-methylphenylamino)propionic acid and 4.08 g (9 mmol) of zirconium(IV) n-propoxide (Fluka, zirconium content 20%) in 50 ml of dry toluene. Analysis found: Zr 16.28%; C 50.77%; H 7.4%; N 2.93%.

EXAMPLE 24

Preparation of the zirconium complex of benzoic acid with zirconium carbonate (compound (124)).

A suspension of 20.76 g (170 mmol) of benzoic acid and 32.74 g (118 mmol) of basic zirconium carbonate (zirconium content 32.88%) in 67 ml of 2-butanol and 100 ml of water is stirred at 75°–80° C. for 3 hours. The suspension is then poured into 162 g of ice and 58 g of water, while stirring vigorously (Ultra-Turrax), and the precipitate is filtered off, washed with a little water and dried in a vacuum drying cabinet (100 mbar) at 80° C. for 15 hours. 31.5 g of the zirconium complex of benzoic acid (compound (124)) result as a white powder. Analysis found: Zr 30.7%; C 38.6%; H 3.1%; $H_2O$ 2.7%.

EXAMPLE 25

Preparation of the zirconium complex of 4-methylbenzoic acid with zirconium carbonate (compound (125)).

30.14 g of the zirconium complex of 4-methylbenzoic acid (compound (125)) are obtained as a white powder analogously to Example 24 from 21.05 g (150 mmol) of 4-methylbenzoic acid, 28.8 g (104 mmol) of zirconium carbonate, 47 g of 2-butanol and 88 ml of water. Analysis found: Zr 27.8%; C 44.1%; H 3.8%; $H_2O$ 1.3%.

EXAMPLE 26

Preparation of the zirconium complex of phenylacetic acid with zirconium carbonate (compound (126)).

26.96 g of the zirconium complex of phenylacetic acid (compound (126)) are obtained as a white powder analogously to Example 24 from 20.42 g (150 mmol) of phenylacetic acid, 28.85 g (104 mmol) of zirconium carbonate, 59 ml of 2-butanol and 88 ml of water. Analysis found: Zr 29.85%; C 40.32%; H 3.65%; $H_2O$ 2.97%.

EXAMPLE 27

Preparation of the zirconium complex of 4-nitrobenzoic acid with zirconium carbonate (compound (127)).

27.73 g of the zirconium complex of 4-nitrobenzoic acid (compound (127)) are obtained as a yellow powder analogously to Example 24 from 20.05 g (120 mmol) of 4-nitrobenzoic acid, 23.03 g (83 mmol) of zirconium carbonate, 47 ml of 2-butanol and 70 ml of water. Analysis found: Zr 18.03%; C 32.16%; H 2.36%; N 5.21%; $H_2O$ 4.17%.

EXAMPLE 28

Preparation of the zirconium complex of 2-hydroxybenzoic acid (salicylic acid) with zirconium carbonate (compound (128)).

29.61 g of the zirconium complex of 2-hydroxybenzoic acid (compound (128)) are obtained as a yellowish powder analogously to Example 24 from 20.72 g (150 mmol) of 2-hydroxybenzoic acid, 28.85 g (104 mmol) of zirconium carbonate, 59 ml of 2-butanol and 88 ml of water. Analysis found: Zr 28.24%; C 35.9%; H 2.9%; $H_2O$ 3.2%.

EXAMPLE 29

Preparation of the zirconium complex of 4-chlorobenzoic acid with zirconium carbonate (compound (129)).

30.75 g of the zirconium complex of 4-chlorobenzoic acid (compound (129)) are obtained as a white powder analogously to Example 24 from 21.92 g (140 mmol) of 4-chlorobenzoic acid, 26.91 g (97 mmol) of zirconium carbonate, 55 ml of 2-butanol and 82 ml of water. Analysis found: Zr 24.91%; C 34.3%; H 2.3%; $H_2O$ 1.9%.

EXAMPLE 30

Preparation of the zirconium complex of naphthenic acid with zirconium n-propoxide (compound (130)).

41.8 g of the zirconium complex of naphthenic acid (compound (130)) are obtained as an orange oil analogously to Example 2 from 20 g (79 mmol) of naphthenic acid [Fluka, mixed aliphatic carboxylic acids, cf. "Dictionary of Organic Compounds", 5th Edition, Volume 4, page 4152 (1982)] and 36 g (79 mmol) of zirconium(IV) n-propoxide (Fluka, zirconium content 20%) in 200 ml of dry toluene. Analysis found: Zr 17.46%; C 54.94%; H 9.33%.

EXAMPLE 31

Preparation of the zirconium complex of 3-hydroxynaphthalene-2-carboxylic acid with zirconium carbonate (compound (131)).

33.67 g of the zirconium complex of 3-hydroxynaphthalene-2-carboxylic acid (compound (131)) are obtained as a yellow powder analogously to Example 24 from 23.7 g (120 mmol) of 3-hydroxynaphthalene-2-carboxylic acid, 23.03 g (83 mmol) of zirconium carbonate, 47 ml of 2-butanol and 70 ml of water. Analysis found: Zr 19.65%; C 46.66%; H 3.6%; $H_2O$ 0.8%.

EXAMPLE 32

Preparation of the zirconium complex of succinic acid with zirconium carbonate (compound (132)).

22.35 g of the zirconium complex of succinic acid (compound (132)) are obtained as a white powder analogously to Example 24 from 20.08 g (170 mmol) of succinic acid, 32.74 g (118 mmol) of zirconium carbonate, 54 g of 2-butanol and 100 ml of water. Analysis found: Zr 43.96%; C 16.78%; H 2.5%; $H_2O$ 0.7%.

EXAMPLE 33

Preparation of the zirconium complex of sebacic acid with zirconium carbonate (compound (133)).

34.1 g of the zirconium complex of sebacic acid (compound (133)) are obtained as a beige powder analogously to Example 24 from 20.23 g (100 mmol) of sebacic acid, 35.8 g (129 mmol) of zirconium carbonate, 73 ml of 2-butanol and 109 ml of water. Analysis found: Zr 30.78%; C 32.9%; H 5.2%; $H_2O$ 1.6%.

EXAMPLE 34

Preparation of the zirconium complex of maleic acid with zirconium carbonate (compound (134)).

25.75 g of the zirconium complex of maleic acid (compound (134)) are obtained as a white powder analogously to Example 24 from 20.89 g (180 mmol) of maleic acid, 34.56 g (125 mmol) of zirconium carbonate, 70 ml of 2-butanol and 106 ml of water. Analysis found: Zr 38.64%; C 15.1%; H 2.6%; H$_2$O 7.6%.

EXAMPLE 35

Preparation of the zirconium complex of phthalic acid with zirconium carbonate (compound (135)).

25.7 g of the zirconium complex of phthalic acid (compound (135)) are obtained as a white powder analogously to Example 24 from 19.94 g (120 mmol) of phthalic acid, 23.03 g (83 mmol) of zirconium carbonate, 47 ml of 2-butanol and 70 ml of water. Analysis found: Zr 27.7%; C 35.4%; H 2.6%; H$_2$O 1.7%.

EXAMPLE 36

Preparation of the zirconium complex of 3-nitro-iso-phthalic acid with zirconium carbonate (compound (136)).

33.03 g of the zirconium complex of 3-nitro-iso-phthalic acid (compound (136)) are obtained as a beige powder analogously to Example 24 from 20.06 g (95 mmol) of 3-nitro-iso-phthalic acid, 34.12 g (123 mmol) of zirconium carbonate, 69 ml of 2-butanol and 104 ml of water. Analysis found: Zr 29.6%; C 22.8%; H 2.3%; N 3.2%; H$_2$O 4.6%.

EXAMPLE 37

Preparation of the zirconium complex of mandelic acid with zirconium carbonate (compound (137)).

27.65 g of the zirconium complex of mandelic acid (compound (137)) are obtained as a beige powder analogously to Example 24 from 23.29 g (150 mmol) of mandelic acid, 28.85 g (104 mmol) of zirconium carbonate, 59 ml of 2-butanol and 88 ml of water. Analysis found: Zr 27.08%; C 39.48%; H 3.6%; H$_2$O 3.7%.

EXAMPLE 38

Preparation of the zirconium complex of benzothiazole-2-thioylsuccinic acid with zirconium carbonate (compound 138)).

65.6 g of the zirconium complex of benzothiazole-2-thioylsuccinic acid (compound (138)) are obtained as a yellowish powder analogously to Example 24 from 80.28 g (170 mmol) of benzothiazole-2-thioylsuccinic acid (content 60%), 34.53 g (118 mmol) of basic zirconium carbonate (zirconium content 31.17%), 67 ml of 2-butanol and 100 ml of water. Analysis found: Zr 16.75%; C 33.85%; H 3.0%; N 3.48%; S 16.01%; H$_2$O 0.53%.

EXAMPLE 39

Preparation of the zirconium complex of benzoic acid with zirconium carbonate (compound (139)).

20.59 g of the zirconium complex of benzoic acid (compound (139)) are obtained as a white powder analogously to Example 24 from 9.77 g (80 mmol) of benzoic acid, 23.41 g (80 mmol) of basic zirconium carbonate (zirconium content 31.17%), 45 ml of 2-butanol and 68 ml of water. Analysis found: Zr 35.43%; C 32.33%; H 2.83%.

EXAMPLE 40

Preparation of the zirconium complex of benzoic acid with zirconium carbonate (compound (140)).

21.01 g of the zirconium complex of benzoic acid (compound (140)) is obtained as a white powder analogously to Example 24 from 10.75 g (88 mmol) of benzoic acid, 23.41 g (80 mmol) of basic zirconium carbonate (zirconium content 31.17%), 45 ml of 2-butanol and 68 ml of water. Analysis found: Zr 34.45%; C 33.90%; H 2.98%; H$_2$O 4.10%.

EXAMPLE 41

Preparation of the zirconium complex of benzoic acid with zirconium carbonate (compound (141)).

21.84 g of the zirconium complex of benzoic acid (compound (141)) is obtained as a white powder analogously to Example 24 from 11.72 g (96 mmol) of benzoic acid, 23.41 g (80 mmol) of basic zirconium carbonate (zirconium content 31.17%), 45 ml of 2-butanol and 68 ml of water. Analysis found: Zr 33.40%; C 35.40%; H 3.05%; H$_2$O 3.30%.

EXAMPLE 42

Preparation of the zirconium complex of benzoic acid with zirconium carbonate (compound (142)).

22.62 g of the zirconium complex of benzoic acid (compound (142)) are obtained as a white powder analogously to Example 24 from 12.7 g (104 mmol) of benzoic acid, 23.41 g (80 mmol) of basic zirconium carbonate (zirconium content 31.17%), 45 ml of 2-butanol and 68 ml of water. Analysis found: Zr 32.31%; C 36.79%; H 3.10%; H$_2$O 3.06%.

EXAMPLE 43

Preparation of the zirconium complex of benzoic acid with zirconium carbonate (compound (143)).

26.86 g of the zirconium complex of benzoic acid (compound (143)) is obtained as a white powder analogously to Example 24 from 19.54 g (160 mmol) of benzoic acid, 23.41 g (80 mmol) of basic zirconium carbonate (zirconium content 31.17%), 45 ml of 2-butanol and 68 ml of water. Analysis found: Zr 27.29%; C 42.74%; H 3.03%.

EXAMPLE 44

Testing of the titanium and zirconium complexes as corrosion inhibitors in an acrylic dispersion based on Maincote HG-54.

To prepare the coating composition based on Maincote HG-54, components 1 to 8 (formulation without additives) or components 1 to 9 (formulation comprising the corrosion inhibitors) are employed in the sequence shown (cf. Table 1).

TABLE 1

| Acrylic dispersion on Maincote HG-54 | |
| --- | --- |
| Composition | % by weight |
| 1) Deionized water | 3.10 |
| 2) Methylcarbitol[a] | 5.00 |
| 3) Orotan 165[b] | 0.82 |
| 4) Triton CF 10[c] | 0.29 |
| 5) Drew Plus TS 4380[d] | 0.28 |
| 6) Acrysol RM 8[e] | 0.60 |
| 7) Bayferrox 130 M[f] | 5.72 |
| 8) Millicarb[g] | 17.40 |
| 9) corrosion inhibitor according to the invention | |
| 10) Butyldiglycol | 3.67 |
| 11) Maincote HG-54[h] | 58.70 |
| 12) Texanol[i] | 1.50 |

TABLE 1-continued

Acrylic dispersion on Maincote HG-54

| Composition | % by weight |
|---|---|
| 13) Dibutyl phthalate[k] | 1.50 |
| 14) Sodium nitrite (13.8% in $H_2O$)[l] | 0.80 |
| 15) Drew T 4310[m] | 0.32 |
| 16) Ammonia solution (25%) | 0.30 |
| Total | 100.0 |

Total solids: 47%; pH: 8 to 8.5;
[a]® Methylcarbitol: diethylene glycol monomethyl ether (Union Carbide);
[b]® Orotan 165? dispersing auxiliary (Rohm & Haas);
[c]® Triton CF 10: nonionic wetting agent (Rohm & Haas);
[d]® Drew Plus TS 4380: defoamer (Drew Chem. Corp.);
[e]® Acrysol RM 8: nonionic thickener (Rohm & Haas);
[f]® Bayferrox 130 M: iron oxide red (Bayer AG);
[g]® Millicarb: calcium carbonate (Omya);
[h]® Maincote HG-54: acrylic dispersion, 41.5% in deionized water (Rohm & Haas);
[i]® Texanol: coalescent (Eastman Chem. Prod., Inc.);
[k]dibutyl phthalate: plasticizer (Eastman Chem. Prod., Inc.);
[l]sodium nitrite: rust film inhibitor (Fluka);
[m]® Drew T 4310: nonionic Components 1 to 8 or 1 to 9 are dispersed to a grinding fineness or grinding particle size of <15 μm using a high-speed stirrer at 3000 revolutions/minute. The dispersing result of the pigment paste thus obtained is evaluated by determination of the grindometer value (ISO 1524). The amount of corrosion inhibitors according to the invention employed is based on the total solids of the formulation without the additive (total solids: 47%). Accordingly, for example, addition of 1% of corrosion inhibitor in 100 g of dispersion means an amount of 0.47 g. To finish the coating composition, components 10 to 16 according to Table 1 are added in the sequence shown at a reduced stirring speed (1000 revolutions/minute). The pH of the formulation is then checked, and if necessary adjusted to a value of pH 8 to 8.5 with ammonia solution (25%) before the application.

The coating composition can be applied in undiluted form by airless spraying, brushing, rolling or, after dilution, by conventional spraying. Dilution to the desired spraying viscosity is effected by addition of butylglycol/water (1:1 g/g). In the present example, the coating composition is applied by conventional spraying.

The formulation is applied to steel sheets (19 times 10.5 cm) of the Bonder type (cold-rolled, degreased steel; producer: Chemetall, Frankfurt am Main, Germany) in a coating thickness, after drying, of 50–55 μm (drying conditions: 10 days at room temperature).

Before the start of weathering, defined damage (70 times 0.5 mm) in the form of a parallel cut (i.e. parallel to the longest edge of the sheet) is caused to the "paint films" using a Bonder cross-cutter (model 205; manufacturer/distributor: Lau, 5870 Hemer/Germany). The edges of the sheet are protected by applying an edge protection (®Icosit 255; manufacturer: Inertol AG, Winterthur, Switzerland).

The specimens are then subjected to accelerated weathering in the salt spray test (DIN 50 021 SS) for 168 hours and in the condensation water test (ASTM D 4585-87) for 330 hours. The results are summarized in Tables 2 and 3. The results are evaluated on the basis of the relevant DIN standards according to a rating code by stating a corrosion protection value CPF ("Corrosion Protection Factor). The CPF is composed additively of an evaluation of the coating (film) and an evaluation of the steel and is 12 points maximum. The individual maximum values for the coating (film) and the steel are 6 points. The higher the numbers, the better the corrosion protection.

As a further evaluation criterion, when the salt spray test has ended, the "subfilm corrosion in the damp state" (cathodic delamination) is determined in accordance with DIN 53 167 along the damage site caused. The less the delamination, the more effective the corrosion inhibitor tested. When the condensation water test has ended, the wet adhesion of the paint formulations is determined with the tape peel-off test in accordance with DIN 53 151 by application of a cross-hatch. According to DIN 53 151 (scale of Gt 0 to Gt 5), a cross-hatch value of Gt 0 corresponds to completely intact adhesion of the paint film, while Gt 5 corresponds to inadequate adhesion.

TABLE 2

Salt spray test, 168 hours

| Compound | CPF film | CPF metal | CPF | Cathodic delamination (mm total) |
|---|---|---|---|---|
| — | 3.0 | 2.0 | 5.0 | 100 |
| 1% (101) | 4.2 | 4.7 | 7.7 | 33 |
| 2% (101) | 4.4 | 5.8 | 10.2 | 22 |
| 1% (102) | 4.4 | 4.0 | 8.4 | 50 |
| 2% (102) | 4.2 | 3.4 | 7.6 | 40 |
| 1% (103) | 3.4 | 5.0 | 8.4 | 70 |
| 2% (103) | 4.2 | 5.0 | 9.2 | 30 |
| 1% (104) | 3.4 | 3.6 | 7.0 | 60 |
| 2% (104) | 4.2 | 3.6 | 7.8 | 30 |
| 1% (105) | 3.4 | 3.6 | 7.0 | 72 |
| 2% (105) | 4.4 | 3.2 | 7.6 | 36 |
| 1% (106) | 4.4 | 4.2 | 8.6 | 64 |
| 2% (106) | 3.4 | 5.0 | 8.4 | 26 |
| 1% (107) | 4.4 | 3.2 | 7.6 | 50 |
| 2% (107) | 4.2 | 3.2 | 7.6 | 36 |
| 1% (109) | 4.2 | 3.0 | 7.2 | 64 |
| 2% (109) | 4.2 | 4.0 | 8.2 | 34 |
| 1% (111) | 4.6 | 4.4 | 9.0 | 100 |
| 2% (111) | 3.6 | 4.4 | 8.0 | 46 |
| 1% (112) | 4.4 | 5.0 | 9.4 | 12 |
| 2% (112) | 4.4 | 5.6 | 10.0 | 9 |
| — | 3.0 | 2.0 | 5.0 | 100 |
| 1% (113) | 4.2 | 2.8 | 7.0 | 46 |
| 2% (113) | 4.4 | 5.6 | 10.0 | 12 |
| 1% (114) | 2.8 | 3.0 | 7.0 | 100 |
| 2% (114) | 3.8 | 3.4 | 7.2 | 48 |
| 1% (115) | 4.3 | 4.5 | 8.8 | 14 |
| 2% (115) | 4.2 | 4.8 | 9.0 | 14 |
| 1% (116) | 4.6 | 4.9 | 9.4 | 13 |
| 2% (116) | 4.6 | 5.7 | 10.3 | 8 |
| 1% (117) | 4.4 | 3.6 | 8.0 | 14 |
| 2% (117) | 4.2 | 5.2 | 9.4 | 17 |
| 1% (118) | 3.0 | 3.0 | 6.0 | 45 |
| 2% (118) | 4.0 | 3.0 | 7.0 | 18 |
| 1% (120) | 3.4 | 3.8 | 7.2 | 12 |
| 2% (120) | 3.5 | 5.2 | 8.7 | 9 |
| 1% (121) | 2.8 | 3.0 | 5.8 | 32 |
| 2% (121) | 4.1 | 3.4 | 7.5 | 25 |
| 1% (123) | 3.7 | 5.0 | 8.7 | 14 |
| 2% (123) | 3.7 | 5.0 | 8.7 | 9 |
| 2% (138) | 4.2 | 5.5 | 9.7 | 16 |
| — | 3.0 | 2.0 | 5.0 | 100 |
| 1% (139) | 4.3 | 5.0 | 9.3 | 30 |
| 2% (139) | 4.3 | 5.6 | 9.9 | 20 |
| 1% (140) | 4.3 | 4.0 | 8.3 | 35 |
| 1% (141) | 4.3 | 4.8 | 9.1 | 33 |
| 1% (142) | 4.3 | 5.0 | 9.3 | 27 |
| 1% (143) | 4.2 | 5.0 | 9.2 | 32 |

TABLE 3

Condensation water test, 330 hours

| Compound | CPF film | CPF metal | CPF | Wet adhesion (Gt value) |
|---|---|---|---|---|
| — | 3.2 | 1.6 | 4.8 | 5 |
| 1% (103) | 5.4 | 6.0 | 11.4 | 1 |
| 2% (103) | 5.4 | 6.0 | 11.4 | 0–1 |
| 1% (104) | 4.6 | 4.4 | 9.0 | 2 |
| 2% (104) | 4.8 | 4.4 | 9.2 | 0 |
| 1% (105) | 4.8 | 4.4 | 9.2 | 2 |
| 2% (105) | 5.0 | 4.8 | 9.8 | 0 |
| 1% (106) | 5.2 | 5.2 | 10.4 | 0–1 |
| 2% (106) | 6.0 | 6.0 | 12.0 | 0–1 |
| 1% (110) | 3.6 | 4.0 | 7.6 | 1 |
| 2% (110) | 6.0 | 5.5 | 11.5 | 0–1 |
| 1% (111) | 4.4 | 5.3 | 9.7 | 1 |
| 2% (111) | 4.6 | 5.8 | 10.4 | 0 |
| 1% (112) | 6.0 | 5.8 | 11.8 | 0–1 |
| 2% (112) | 6.0 | 6.0 | 12.0 | 0–1 |
| 1% (113) | 6.0 | 5.5 | 11.5 | 0–1 |
| 2% (113) | 6.0 | 5.8 | 11.8 | 1 |
| 1% (114) | 5.2 | 4.0 | 9.2 | 1–2 |
| 2% (114) | 6.0 | 5.8 | 11.8 | 0–1 |
| 1% (115) | 5.5 | 5.3 | 10.8 | 0 |
| 2% (115) | 6.0 | 5.0 | 11.0 | 0 |
| — | 3.2 | 1.6 | 4.8 | 5 |
| 1% (116) | 5.4 | 5.2 | 10.6 | 0 |
| 2% (116) | 5.4 | 5.5 | 10.9 | 0 |
| 1% (117) | 3.0 | 2.6 | 5.6 | 0–1 |
| 2% (117) | 3.2 | 5.5 | 8.7 | 0–1 |
| 1% (119) | 4.8 | 5.0 | 9.8 | 0 |
| 2% (119) | 5.0 | 5.7 | 10.7 | 0 |
| 1% (120) | 5.5 | 4.8 | 10.3 | 0 |
| 2% (120) | 5.0 | 5.7 | 10.7 | 0 |
| 1% (123) | 4.8 | 5.0 | 9.8 | 0 |
| 2% (123) | 5.2 | 5.5 | 10.7 | 0 |
| 2% (139) | 4.6 | 6.0 | 10.6 | 0 |
| 1% (141) | 4.0 | 4.7 | 8.7 | 1 |

EXAMPLE 45

Testing of the titanium and zirconium complexes as corrosion inhibitors in an acrylic dispersion based on Maincote HG-54.

To prepare the coating composition based on Maincote HG-54, components 1 to 16 are employed in the sequence shown, analogously to Example 44 (cf. Table 1).

The formulation is applied analogously to Example 44 to steel sheets (19 times 10.5 cm) of the Bonder type (cold-rolled, degreased steel; producer: Chemetall, Frankfurt am Main, Germany). In contrast to Example 44, the coating thickness after drying is not 50–55 μm but 60–65 μm (drying conditions: 10 days at room temperature).

The salt spray test (290 hours) and condensation water test (330 hours) and the determination of the corrosion protection values CPF are carried out as described in Example 44. The results are summarized in Tables 4 and 5. The higher the numbers, the better the corrosion protection.

As a further evaluation criterion, when the salt spray test has ended, the "subfilm corrosion in the damp state" (cathodic delamination) is determined in accordance with DIN 53 167 along the damage caused, analogously to Example 44. The less the delamination, the more effective the corrosion inhibitor tested. When the condensation water test has ended, the wet adhesion of the paint formulations is determined with the tape peeling test in accordance with DIN 53 151 by application of a cross-hatch. According to DIN 53 151 (scale of Gt 0 to Gt 5), a cross-hatch value of Gt 0 corresponds to a completely intact adhesion of the paint film, while Gt 5 corresponds to inadequate adhesion.

TABLE 4

Salt spray test, 290 hours

| Compound | CPF film | CPF metal | CPF | Cathodic delamination (mm total) |
|---|---|---|---|---|
| — | 3.0 | 3.4 | 6.4 | 100 |
| 1% (125) | 4.0 | 5.0 | 9.0 | 55 |
| 2% (125) | 4.2 | 5.8 | 10.0 | 31 |
| 1% (126) | 4.0 | 5.5 | 9.5 | 31 |
| 1% (128) | 4.2 | 5.0 | 9.2 | 31 |
| 1% (129) | 4.0 | 6.0 | 10.0 | 43 |
| 2% (129) | 4.4 | 5.5 | 9.9 | 10 |
| 1% (133) | 2.6 | 6.0 | 8.6 | 100 |
| 2% (133) | 3.3 | 5.8 | 9.1 | 18 |
| 1% (135) | 4.8 | 5.8 | 10.6 | 44 |
| 1% (136) | 4.2 | 5.8 | 10.0 | 70 |
| 2% (136) | 4.0 | 5.0 | 10.0 | 34 |

TABLE 5

Condensation water test, 330 hours

| Compound | CPF film | CPF metal | CPF | Wet adhesion (Gt value) |
|---|---|---|---|---|
| — | 3.2 | 2.0 | 5.2 | 5 |
| 1% (124) | 5.8 | 6.0 | 11.8 | 0–1 |
| 2% (124) | 6.0 | 6.0 | 12.0 | 0 |
| 1% (125) | 5.9 | 6.0 | 11.9 | 0 |
| 2% (125) | 5.9 | 6.0 | 11.9 | 0 |
| 1% (126) | 5.8 | 6.0 | 11.8 | 1 |
| 1% (127) | 5.4 | 6.0 | 11.4 | 0 |
| 2% (127) | 6.0 | 6.0 | 12.0 | 0–1 |
| 1% (129) | 5.9 | 6.0 | 11.9 | 0 |
| 2% (129) | 6.0 | 6.0 | 12.0 | 0 |
| 1% (130) | 5.4 | 5.6 | 11.0 | 0–1 |
| 2% (130) | 5.8 | 5.4 | 11.2 | 0–1 |
| 1% (133) | 6.0 | 6.0 | 12.0 | 0–1 |
| 2% (133) | 6.0 | 6.0 | 12.0 | 0–1 |
| 1% (135) | 6.0 | 6.0 | 12.0 | 0 |
| 1% (136) | 4.8 | 6.0 | 10.8 | 1 |
| 2% (136) | 6.0 | 6.0 | 12.0 | 0 |
| 1% (137) | 3.4 | 5.8 | 9.2 | 1 |
| 2% (137) | 5.0 | 6.0 | 11.0 | 1 |

What is claimed is:

1. A coating composition comprising
a) an organic film-forming binder and
b) a corrosion inhibiting amount of, at least one titanium or zirconium complex of a compound of the formula I

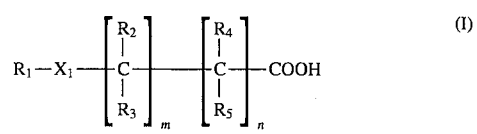

in which
$R_1$ is hydrogen, $C_1$–$C_{25}$alkyl, $C_2$–$C_{25}$alkyl which is interrupted by oxygen, sulfur or >N—$R_6$; $C_2$–$C_{24}$alkenyl, $C_4$–$C_{15}$cycloalkyl which is unsubstituted or substituted by $C_1$–$C_4$alkyl; $C_5$–$C_{15}$cycloalkenyl which is unsubstituted or substituted by $C_1$–$C_4$alkyl; $C_{13}$–$C_{26}$polycycloalkyl, $C_7$–$C_9$phenylalkyl which is unsubstituted or substituted on the phenyl ring by $C_1$–$C_4$alkyl; —$COR_7$, a 5- or 6-membered heterocyclic ring which is unsubstituted or substituted by $C_1$–$C_4$alkyl, $C_1$–$C_4$alkoxy, halogen or carboxyl; a benzo-fused 5- or 6-membered heterocyclic ring which is unsubstituted or substituted by $C_1$–$C_4$alkyl, $C_1$–$C_4$alkoxy, halogen or carboxyl; or $R_1$ furthermore is a radical of the formula II, III or IV

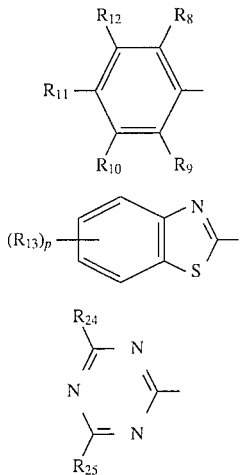

$R_2$, $R_3$, $R_4$ and $R_5$ independently of one another are hydrogen, hydroxyl, $C_1$–$C_{18}$alkoxy, $C_2$–$C_{18}$alkoxy which is interrupted by oxygen, sulfur or $>$N—$R_6$;

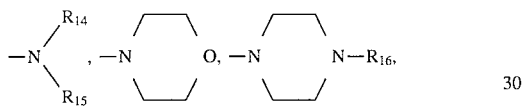

$C_1$–$C_{25}$alkyl, $C_2$–$C_{25}$alkyl which is interrupted by oxygen, sulfur or $>$N—$R_6$; $C_2$–$C_{24}$alkenyl, $C_5$–$C_{24}$alkenyl, $C_5$–$C_{15}$cycloalkyl which is unsubstituted or substituted by $C_1$–$C_4$alkyl; $C_5$–$C_{15}$cycloalkenyl which is unsubstituted or substituted by $C_1$–$C_4$alkyl; phenyl or naphthyl which are unsubstituted or substituted by $C_1$–$C_4$alkyl; $C_7$–$C_9$phenylalkyl which is unsubstituted or substituted on the phenyl ring by $C_1$–$C_4$alkyl; $C_{10}$–$C_{12}$naphthylalkyl which is unsubstituted or substituted on the naphthyl ring by $C_1$–$C_4$alkyl; or —COR$_7$, with the proviso that if one of the radical $R_2$, $R_3$, $R_4$ or $R_5$ is hydroxyl,

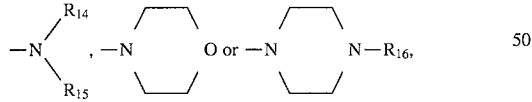

the other radical bonded to the same C atom is other than hydroxyl,

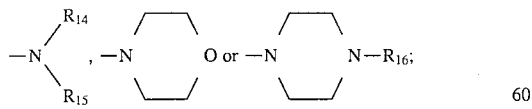

or $R_2$ and $R_3$ or $R_4$ and $R_5$ furthermore, together with the C atom to which they are bonded, form a $C_5$–$C_{12}$cycloalkylidene ring which is unsubstituted or substituted by $C_1$–$C_4$alkyl, $R_6$ is hydrogen or $C_1$–$C_8$alkyl, $R_7$ is hydroxyl, $C_1$–$C_{18}$alkoxy, $C_2$–$C_{18}$alkoxy which is interrupted by oxygen, sulfur or

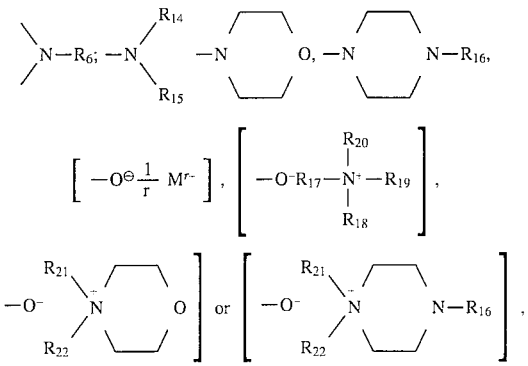

$R_8$, $R_9$, $R_{10}$, $R_{11}$ and $R_{12}$ independently of one another are hydrogen, hydroxyl, halogen, nitro,

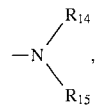

cyano, CF$_3$, —COR$_7$, $C_1$–$C_{25}$alkyl, $C_2$–$C_{25}$alkyl which is interrupted by oxygen, sulfur or $>$N—$R_6$; $C_1$–$C_{25}$halogenoalkyl, $C_1$–$C_{18}$alkoxy, $C_2$–$C_{18}$alkoxy which is interrupted by oxygen, sulfur or $>$N—$R_6$; $C_1$–$C_{18}$alkylthio, $C_2$–$C_{24}$alkenyl, $C_5$–$C_{15}$cycloalkyl which is unsubstituted or substituted by $C_1$–$C_4$alkyl; $C_5$–$C_{15}$cycloalkenyl which is unsubstituted or substituted by $C_1$–$C_4$alkyl; phenyl or naphthyl which are unsubstituted or substituted by $C_1$–$C_4$alkyl; $C_7$–$C_9$phenylalkyl which is unsubstituted or substituted on the phenyl ring by $C_1$–$C_4$alkyl; $C_{10}$–$C_{12}$naphthylalkyl which is unsubstituted or substituted on the naphthyl ring by $C_1$–$C_4$alkyl; phenoxy or naphthoxy which are unsubstituted or substituted by $C_1$–$C_4$alkyl; $C_7$–$C_9$-phenylalkoxy which is unsubstituted or substituted on the phenyl ring by $C_1$–$C_4$alkyl; $C_{10}$–$C_{12}$naphthylalkoxy which is unsubstituted or substituted on the naphthyl ring by $C_1$–$C_4$alkyl; or the radicals $R_9$ and $R_{10}$ or the radicals $R_{10}$ and $R_{11}$ or the radicals $R_{11}$ and $R_{12}$ or the radicals $R_8$ and $R_{12}$ furthermore, together with the carbon atoms to which they are bonded, form a benzo ring which is unsubstituted or substituted by $C_1$–$C_4$alkyl, halogen or $C_1$–$C_4$alkoxy, $R_{13}$ is hydrogen, hydroxyl, halogen, nitro, cyano, CF$_3$, $C_1$–$C_{25}$alkyl, $C_2$–$C_{25}$alkyl which is interrupted by oxygen, sulfur or $>$N—$R_6$; $C_1$–$C_{25}$halogenoalkyl, $C_1$–$C_{18}$alkoxy, $C_2$–$C_{18}$alkoxy which is interrupted by oxygen, sulfur or $>$N—$R_6$; $C_1$–$C_{18}$alkylthio or $C_2$–$C_{24}$alkenyl;

$R_{14}$ and $R_{15}$ independently of one another are hydrogen, $C_1$–$C_{25}$alkyl, $C_2$–$C_{25}$alkyl which is interrupted by oxygen, sulfur or $>$N—$R_6$; $C_2$–$C_{24}$alkenyl, $C_5$–$C_{15}$cycloalkyl which is unsubstituted or substituted by $C_1$–$C_4$alkyl; phenyl or naphthyl which are unsubstituted or substituted by $C_1$–$C_4$alkyl, $R_{16}$ is hydrogen or $C_1$–$C_{18}$alkyl, $R_{17}$, $R_{18}$, $R_{19}$, $R_{20}$, $R_{21}$ and $R_{22}$ independently of one another are hydrogen or $C_1$–$C_{25}$alkyl, $R_{23}$ is hydrogen, $C_1$–$C_{25}$alkyl, $C_2$–$C_{25}$alkyl which is interrupted by oxygen, sulfur or $>$N—$R_6$; $C_2$–$C_{24}$alkenyl, $C_5$–$C_{15}$cycloalkyl which is unsubstituted or substituted by $C_1$–$C_4$alkyl; phenyl or naphthyl which are unsubstituted or substituted by $C_1$–$C_4$alkyl, $R_{24}$ and $R_{25}$ independently of one another are hydrogen, $C_1$–$C_{25}$alkyl, $C_1$–$C_{18}$alkoxy, —$X_2$—$(CH_2)_sCOR_7$ or

M is an r-valent metal cation, $X_1$ is a direct bond, oxygen, sulfur, —$NR_{23}$—, $C_1$–$C_{18}$alkylene, $C_2$–$C_{18}$alkylene which is interrupted by oxygen, sulfur or >N—$R_6$, $C_2$–$C_{18}$alkenylene, $C_2$–$C_{18}$alkynylene, $C_2$–$C_{20}$alkylidene, $C_7$–$C_{20}$phenylalkylidene or $C_5$–$C_8$cycloalkylene, with the proviso that if m and n are 0, $X_1$ is other than oxygen and sulfur, $X_2$ is oxygen or —$NR_{23}$—, m and n independently of one another are an integer from 0 to 10, p is an integer from 0 to 4, r is 1, 2 or 3, and s is an integer from 1 to 8.

2. A coating composition according to claim 1, in which $R_1$ is hydrogen, $C_1$–$C_{18}$alkyl, $C_2$–$C_{18}$alkyl which is interrupted by oxygen, sulfur or >N—$R_6$; $C_2$–$C_{18}$alkenyl, $C_4$–$C_{15}$cycloalkyl which is unsubstituted or substituted by $C_1$–$C_4$alkyl; $C_5$–$C_{12}$cycloalkenyl which is unsubstituted or substituted by $C_1$–$C_4$alkyl; $C_{13}$–$C_{26}$polycycloalkyl, $C_7$–$C_9$phenylalkyl, —$COR_7$, a 5- or 6- membered heterocyclic ring which is unsubstituted or substituted by $C_1$–$C_4$alkyl, $C_1$–$C_4$alkoxy, chlorine or carboxyl; a benzo-fused 5- or 6-membered heterocyclic ring which is unsubstituted or substituted by $C_1$–$C_4$alkyl, $C_1$–$C_4$alkoxy, chlorine or carboxyl; or $R_1$ furthermore is a radical of the formula II, III or IV

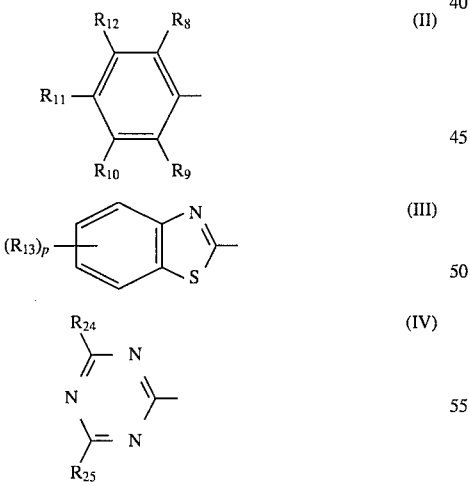

$R_2$, $R_3$, $R_4$ and $R_5$ independently of one another are hydrogen, hydroxyl, $C_1$–$C_{12}$alkoxy, $C_2$–$C_{12}$alkoxy which is interrupted by oxygen or sulfur;

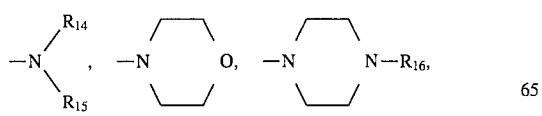

$C_1$–$C_{18}$alkyl, $C_2$–$C_{18}$alkyl which is interrupted by oxygen or sulfur; $C_2$–$C_{18}$alkenyl, $C_5$–$C_{15}$cycloalkyl, $C_5$–$C_{15}$cycloalkenyl, phenyl, naphthyl, $C_7$–$C_9$phenylalkyl, $C_{10}$–$C_{12}$naphthylalkyl or —$COR_7$, with the proviso that if one of the radicals $R_2$, $R_3$, $R_4$ or $R_5$ is hydroxyl,

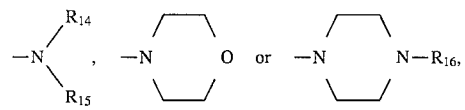

the other radical bonded to the same C atom is other than hydroxyl,

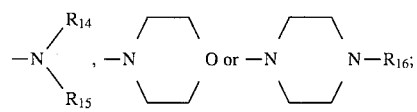

or $R_2$ and $R_3$ or $R_4$ and $R_5$ furthermore, together with the C atom to which they are bonded, form a $C_5$–$C_8$cycloalkylidene ring which is unsubstituted or substituted by $C_1$–$C_4$alkyl, $R_7$ is hydroxyl, $C_1$–$C_{12}$alkoxy, $C_2$–$C_{12}$alkoxy which is interrupted by oxygen or sulfur;

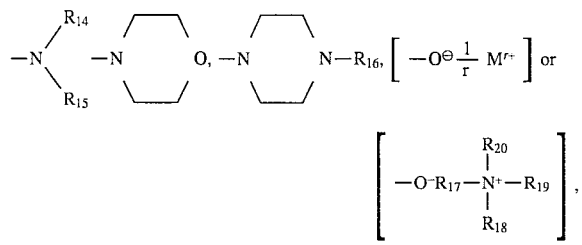

$R_8$, $R_9$, $R_{10}$, $R_{11}$ and $R_{12}$ independently of one another are hydrogen, hydroxyl, halogen, nitro,

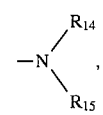

cyano, $CF_3$, —$COR_7$, $C_1$–$C_{18}$alkyl, $C_2$–$C_{18}$alkyl which is interrupted by oxygen or sulfur; $C_1$–$C_{18}$halogenoalkyl, $C_1$–$C_{12}$alkoxy, $C_2$–$C_{12}$alkoxy which is interrupted by oxygen or sulfur; $C_1$–$C_{12}$alkylthio, $C_2$–$C_{18}$alkenyl, $C_5$–$C_{12}$cycloalkyl, $C_5$–$C_{12}$cycloalkenyl, phenyl, naphthyl, $C_7$–$C_9$phenylalkyl, $C_{10}$–$C_{12}$naphthylalkyl, phenoxy, naphthoxy, $C_7$–$C_9$phenylalkoxy or $C_{10}$–$C_{12}$naphthylalkoxy; or the radicals $R_9$ and $R_{10}$ or the radicals $R_{10}$ and $R_{11}$ or the radicals $R_{11}$ and $R_{12}$ or the radicals $R_8$ and $R_{12}$ furthermore, together with the carbon atoms to which they are bonded, form a benzo ring which is unsubstituted or substituted by $C_1$–$C_4$alkyl or chlorine, $R_{13}$ is hydrogen, hydroxyl, halogen, nitro, cyano, $CF_3$, $C_1$–$C_{18}$alkyl which is interrupted by oxygen or sulfur; $C_1$–$C_{18}$halogenoalkyl, $C_1$–$C_{12}$alkoxy, $C_2$–$C_{12}$alkoxy which is interrupted by oxygen or sulfur; $C_1$–$C_{12}$alkylthio or $C_2$–$C_{18}$alkenyl, $R_{14}$ and $R_{15}$ independently of one another are hydrogen, $C_1$–$C_{18}$alkyl, $C_2$–$C_{18}$alkyl which is interrupted by oxygen or sulfur; $C_2$–$C_{18}$alkenyl, $C_5$–$C_{12}$cycloalkyl, phenyl or naphthyl, $R_{16}$ is hydrogen or $C_1$–$C_{12}$alkyl, $R_{17}$, $R_{18}$, $R_{19}$, $R_{20}$, $R_{21}$ and $R_{22}$ independently of one another are hydrogen or $C_1$–$C_{18}$alkyl, $R_{23}$ is hydrogen, $C_1$–$C_{18}$alkyl, $C_2$–$C_{18}$alkyl which is interrupted by oxygen or sulfur; $C_2$–$C_{18}$alkenyl, $C_5$–$C_{12}$cycloalkyl, phenyl or naphthyl, $R_{24}$ and $R_{25}$ independently of one another are hydrogen, $C_1$–$C_{18}$alkyl, $C_1$–$C_{12}$alkoxy,

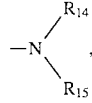

$X_1$ is a direct bond, oxygen, sulfur, —$NR_{23}$—, $C_1$–$C_{12}$alkylene, $C_2$–$C_{12}$alkylene which is interrupted by oxygen or sulfur; $C_2$–$C_{12}$alkenylene, $C_2$–$C_{12}$alkenylene, $C_2$–$C_{16}$alkylidene, $C_7$–$C_{16}$phenylalkylidene or $C_5$–$C_8$cycloalkylene, with the proviso that if m and n are 0, $X_1$ is other than oxygen and sulfur, $X_2$ is —$NR_{23}$—, p is 0, 1 or 2, and s is an integer from 2 to 7.

3. A coating composition according to claim 1, in which $R_1$ is hydrogen, $C_1$–$C_{12}$alkyl, $C_3$–$C_{12}$alkyl which is interrupted by oxygen; $C_2$–$C_{12}$alkenyl, $C_4$–$C_{15}$cycloalkyl, $C_5$–$C_8$cycloalkenyl, $C_{13}$–$C_{26}$polycycloalkyl, benzyl, —$COR_7$, or thienyl, tetrahydrofuranyl, furyl, pyrrolidinyl, pyrrolyl, thiazolyl, isothiazolyl, triazolyl, tetrazolyl, oxazolyl, isoxazolyl, pyridyl, piperidinyl, pyrazinyl, piperazinyl or triazinyl which are unsubstituted or substituted by $C_1$–$C_4$alkyl, $C_1$–$C_4$alkoxy, chlorine or carboxyl or benzo-fused; or $R_1$ furthermore is a radical of the formula II, III or IV

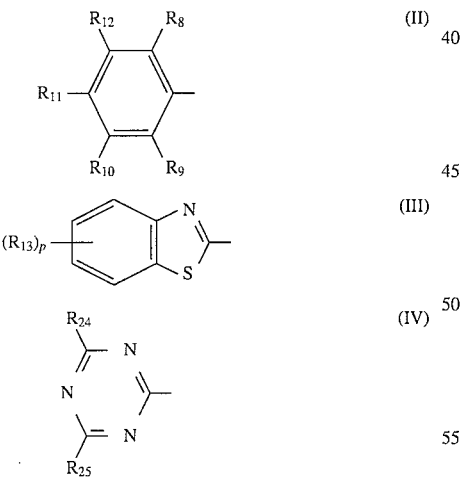

$R_7$ is hydroxyl, $C_1$–$C_{10}$-alkoxy, $C_2$–$C_{12}$alkoxy which is interrupted by oxygen;

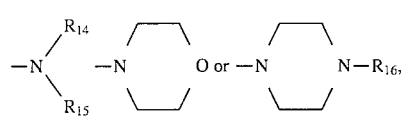

$R_8$, $R_9$, $R_{10}$, $R_{11}$ and $R_{12}$ independently of one another are hydrogen, hydroxyl, chlorine, nitro,

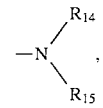

—$COR_7$, $C_1$–$C_{12}$alkyl, $C_2$–$C_{16}$alkyl which is interrupted by oxygen; $C_1$–$C_{12}$halogenoalkyl, $C_1$–$C_{12}$alkoxy, $C_2$–$C_{12}$alkoxy which is interrupted by oxygen; $C_2$–$C_{12}$alkenyl, $C_5$–$C_9$cycloalkyl, $C_5$–$C_9$cycloalkenyl, phenyl, naphthyl, $C_7$–$C_9$phenylalkyl, $C_{10}$–$C_{12}$naphthylalkyl, phenoxy or $C_7$–$C_9$phenylalkoxy; or the radicals $R_9$ and $R_{10}$ or the radicals $R_{10}$ and $R_{11}$ furthermore, together with the carbon atoms to which they are bonded, form a benzo ring, $R_{13}$ is hydrogen, hydroxyl, chlorine, nitro, $C_1$–$C_{12}$alkyl, $C_2$–$C_{12}$alkyl which is interrupted by oxygen; $C_1$–$C_{10}$alkoxy or $C_2$–$C_{10}$alkoxy which is interrupted by oxygen, $R_{14}$ and $R_{15}$ independently of one another are hydrogen, $C_1$–$C_{12}$alkyl, $C_2$–$C_{12}$alkyl which is interrupted by oxygen; $C_5$–$C_9$cycloalkyl or phenyl, $R_{16}$ is hydrogen or $C_1$–$C_8$alkyl, $R_{23}$ is hydrogen, $C_1$–$C_{12}$alkyl, $C_3$–$C_{12}$alkyl which is interrupted by oxygen; $C_2$–$C_{12}$alkenyl, $C_5$–$C_9$cycloalkyl or phenyl, $R_{24}$ and $R_{25}$ independently of one another are hydrogen or —$X_2$—$(CH_2)_sCOR_7$ or

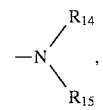

$X_1$ is a direct bond, oxygen, sulfur, —$NR_{23}$—, $C_1$–$C_8$alkylene, $C_2$–$C_8$alkenylene, $C_2$–$C_8$—alkynylene, $C_2$–$C_{12}$alkylidene, $C_7$–$C_{12}$phenylalkylidene or $C_5$–$C_8$cycloalkylene, with the proviso that if m and n are 0, $X_1$ is other than oxygen and sulfur, $X_2$ is —$NR_{23}$—, p is 0 or 1, and s is an integer from 3 to 6.

4. A coating composition according to claim 1, in which $R_2$, $R_3$, $R_4$ and $R_5$ independently of one another are hydrogen, hydroxyl, $C_1$–$C_{10}$alkoxy, $C_2$–$C_{12}$alkoxy which is interrupted by oxygen;

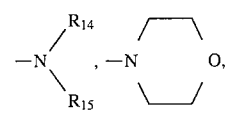

$C_1$–$C_{12}$alkyl, $C_2$–$C_{18}$alkyl which is interrupted by oxygen; $C_2$–$C_{12}$alkenyl, $C_5$–$C_9$cycloalkyl, $C_5$–$C_9$cycloalkenyl, phenyl, naphthyl, $C_7$–$C_9$phenylalkyl or —$COR_7$, with the proviso that if one of the radicals $R_2$, $R_3$, $R_4$ or $R_5$ is hydroxyl,

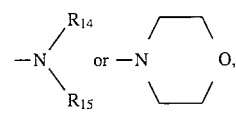

the other radical bonded to the same C atom is other than hydroxyl,

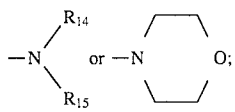

or $R_2$ and $R_3$ or $R_4$ and $R_5$ furthermore, together with the C atom to which they are bonded, form a $C_5$–$C_8$cycloalkylidene ring which is unsubstituted or substituted by $C_1$–$C_4$alkyl, and $R_7$ is hydroxyl, $C_1$–$C_{10}$alkoxy, $C_2$–$C_{12}$alkoxy interrupted by oxygen;

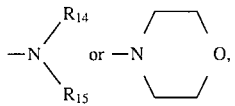

and $R_{14}$ and $R_{15}$ independently of one another are hydrogen, $C_1$–$C_{12}$alkyl, $C_2$–$C_{12}$alkyl which is interrupted by oxygen; $C_5$–$C_9$cycloalkyl or phenyl.

5. A coating composition according to claim 1, in which $R_2$, $R_3$, $R_4$ and $R_5$ independently of one another are hydrogen, hydroxyl, $C_1$–$C_{10}$alkoxy,

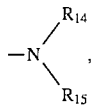

$C_1$–$C_{12}$alkyl, $C_2$–$C_{12}$alkenyl, $C_5$–$C_9$cycloalkyl or $C_5$–$C_9$cycloalkenyl, with the proviso that if one of the radicals $R_2$, $R_3$, $R_4$ or $R_5$ is hydroxyl or

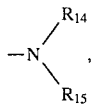

the other radical bonded to the same C atom is other than hydroxyl or

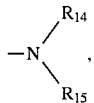

and $R_{14}$ and $R_{15}$ independently of one another are hydrogen or $C_1$–$C_8$alkyl.

6. A coating composition according to claim 1, in which $R_1$ is hydrogen, $C_1$–$C_{12}$alkyl, $C_2$–$C_{12}$alkenyl, $C_4$–$C_{15}$cycloalkyl, $C_{13}$–$C_{26}$polycycloalkyl, benzyl, —$COR_7$, pyrrolidinyl which is unsubstituted or substituted by $C_1$–$C_4$alkyl, $C_1$–$C_4$alkoxy or chlorine; or $R_1$ furthermore is a radical of the formula II or III

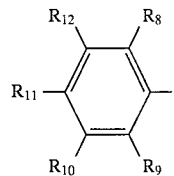

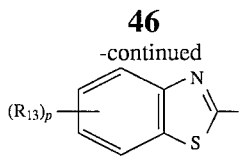

$R_7$ is hydroxyl or $C_1$–$C_{10}$alkoxy, $R_8$, $R_9$, $R_{10}$, $R_{11}$ and $R_{12}$ independently of one another are hydrogen, hydroxyl, chlorine, nitro, —$COR_7$, $C_1$–$C_8$alkyl, $C_1$–$C_4$alkoxy or cyclohexyl; or the radicals $R_9$ and $R_{10}$ or the radicals $R_{10}$ and $R_{11}$ furthermore, together with the carbon atoms to which they are bonded, form a benzo ring, $R_{13}$ is hydrogen, $C_1$–$C_4$ alkyl, chlorine or $C_1$–$C_4$alkoxy, $R_{23}$ is hydrogen, $C_1$–$C_8$alkyl or phenyl, $X_1$ is a direct bond, oxygen, sulfur, —$NR_{23}$— or $C_2$–$C_4$alkenylene, with the proviso that if m and n are 0, $X_1$ is other than oxygen and sulfur, and p is 0 or 1.

7. A coating composition according to claim 1, in which $R_1$ is hydrogen, $C_4$–$C_{15}$cycloalkyl, $C_{13}$–$C_{26}$polycycloalkyl or —$COR_7$; or $R_1$ furthermore is a radical of the formula II or III

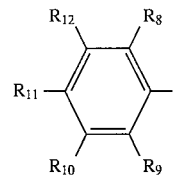

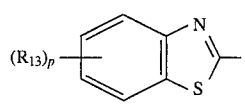

$R_2$, $R_3$, $R_4$ and $R_5$ independently of one another are hydrogen, hydroxyl or —$COR_7$, with the proviso that if one of the radicals $R_2$, $R_3$, $R_4$ or $R_5$ is hydroxyl, the other radical bonded to the same C atom is other than hydroxyl, $R_7$ is hydroxyl, $R_8$ is hydrogen, hydroxyl or —$COR_7$, $R_9$ is hydrogen, $R_{10}$ is hydrogen, $C_1$–$C_4$alkyl or nitro, $R_{11}$ is hydrogen, methyl, nitro or chlorine, or the radicals $R_{10}$ and $R_{11}$, together with the carbon atoms to which they are bonded, form a benzo ring, $R_{12}$ is hydrogen, $C_1$–$C_4$alkyl or —$COR_7$, $R_{23}$ is hydrogen, $X_1$ is a direct bond, oxygen, sulfur, —$NR_{23}$— or vinylene, with the proviso that if m and n are 0, $X_1$ is other than oxygen and sulfur, m is an integer from 0 to 8, n is an integer from 0 to 8, and p is 0.

8. A coating composition according to claim 1, in which the coating composition is a surface-coating material.

9. A coating composition according to claim 1, in which the coating composition is an aqueous surface-coating material.

10. A coating composition according to claim 1, in which component a) is an epoxy resin, a polyurethane resin, a polyester resin, an acrylic resin, an acrylic copolymer resin, a polyvinyl resin, a phenolic resin, an alkyd resin or a mixture of such resins.

11. A coating composition according to claim 1, additionally comprising one or more components from the group consisting of pigments, dyes, fillers, flow control agents, dispersants, thixotropic agents, adhesion promoters, antioxidants, light stabilizers or curing catalysts.

12. A coating composition according to claim 1, in which component b) is present in an amount of 0.01 to 20 %, based on the total solids of the coating composition.

13. A coating composition comprising
a) an organic film-forming binder and
b) a corrosion inhibiting amount of at least one titanium or zirconium complex obtained by reaction of a carboxylic acid of the formula I as defined in claim 1 with a titanium or zirconium compound.

14. A coating composition according to claim 13, in which the molar ratio of the carboxylic acid of the formula I to the titanium or zirconium compound is 20:1 to 1:10.

15. A product obtainable by reaction of a compound of the formula I according to claim 1 or an alkali metal salt thereof with a titanium or zirconium compound.

16. A coating composition comprising
a) an organic film-forming binder and
b) a corrosion inhibiting amount of at least one titanium or zirconium complex obtained by reaction of an alkali metal salt of a carboxylic acid of the formula I as defined in claim 1 with a titanium or zirconium compound.

17. A process for protecting a corrodable metal substrate, which comprises applying a coating composition according to claim 1 to this and then drying and/or curing the coating composition.

18. A titanium or zirconium complex of a compound of the formula I

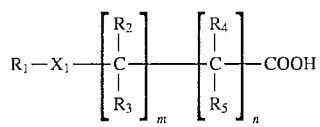

in which $R_1$ is hydrogen, $C_1$–$C_{25}$alkyl, $C_2$–$C_{25}$alkyl which is interrupted by oxygen, sulfur or >N—$R_6$; $C_2$–$C_{24}$alkenyl, $C_4$–$C_{15}$cycloalkyl which is unsubstituted or substituted by $C_1$–$C_4$alkyl; $C_5$–$C_{15}$cycloalkenyl which is unsubstituted or substituted by $C_1$–$C_4$alkyl; $C_{13}$–$C_{26}$polycycloalkyl, $C_7$–$C_9$phenylalkyl which is unsubstituted or substituted on the phenyl ring by $C_1$–$C_4$alkyl; —$COR_7$, a 5- or 6-membered heterocyclic ring which is unsubstituted or substituted by $C_1$–$C_4$alkyl, $C_1$–$C_4$alkoxy, halogen or carboxyl; a benzo-fused 5- or 6-membered heterocyclic ring which is unsubstituted or substituted by $C_1$–$C_4$alkyl, $C_1$–$C_4$alkoxy, halogen or carboxyl; or $R_1$ furthermore is a radical of the formula II, III or IV

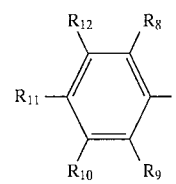

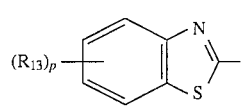

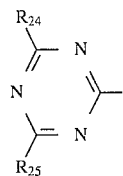

$R_2$, $R_3$, $R_4$ and $R_5$ independently of one another are hydrogen, hydroxyl, $C_1$–$C_{18}$alkoxy, $C_2$–$C_{18}$alkoxy which is interrupted by oxygen, sulfur or >N—$R_6$;

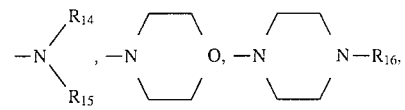

$C_1$–$C_{25}$alkyl, $C_2$–$C_{25}$alkyl which is interrupted by oxygen, sulfur or >N—$R_6$; $C_2$–$C_{24}$alkenyl, $C_5$–$C_{15}$cycloalkyl which is unsubstituted or substituted by $C_1$–$C_4$alkyl; $C_5$–$C_{15}$cycloalkenyl which is unsubstituted or substituted by $C_1$–$C_4$alkyl; phenyl or naphthyl which are unsubstituted or substituted by $C_1$–$C_4$alkyl; $C_7$–$C_9$phenylalkyl which is unsubstituted or substituted on the phenyl ring by $C_1$–$C_4$alkyl; $C_{10}$–$C_{12}$naphthylalkyl which is unsubstituted or substituted on the naphthyl ring by $C_1$–$C_4$alkyl; or —$COR_7$, with the proviso that if one of the radicals $R_2$, $R_3$, $R_4$ or $R_5$ is hydroxyl,

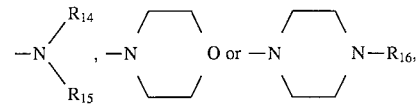

the other radical bonded to the same C atom is other than hydroxyl,

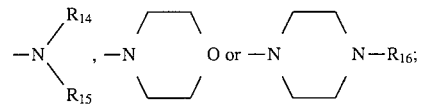

or $R_2$ and $R_3$ or $R_4$ and $R_5$ furthermore, together with the C atom to which they are bonded, form a $C_5$–$C_{12}$cycloalkylidene ring which is unsubstituted or substituted by $C_1$–$C_4$alkyl, $R_6$ is hydrogen or $C_1$–$C_8$alkyl, $R_7$ is hydroxyl, $C_1$–$C_{18}$alkoxy, $C_2$–$C_{18}$alkoxy which is interrupted by oxygen, sulfur or

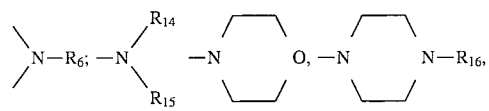

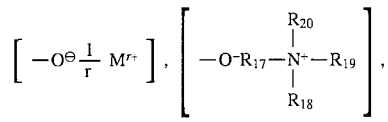

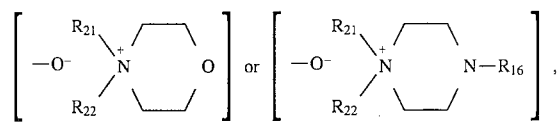

$R_8$, $R_9$, $R_{10}$, $R_{11}$ and $R_{12}$ independently of one another are hydrogen, hydroxyl, halogen, nitro,

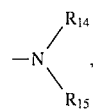

cyano, CF$_3$, —COR$_7$, C$_1$–C$_{25}$alkyl, C$_2$–C$_{25}$alkyl which is interrupted by oxygen, sulfur or >N—R$_6$; C$_1$–C$_{25}$halogenoalkyl, C$_1$–C$_{18}$alkoxy, C$_2$–C$_{18}$alkoxy which is interrupted by oxygen, sulfur or >N—R$_6$; C$_1$–C$_{18}$alkylthio, C$_2$–C$_{24}$alkenyl, C$_5$–C$_{15}$cycloalkyl which is unsubstituted or substituted by C$_1$–C$_4$alkyl; C$_5$–C$_{15}$cycloalkenyl which is unsubstituted or substituted by C$_1$–C$_4$ alkyl; phenyl or naphthyl which are unsubstituted or substituted by C$_1$–C$_4$alkyl; C$_7$–C$_9$phenylalkyl which is unsubstituted or substituted on the phenyl ring by C$_1$–C$_4$alkyl; C$_{10}$–C$_{12}$naphthylalkyl which is unsubstituted or substituted on the naphthyl ring by C$_1$–C$_4$alkyl; phenoxy or naphthoxy which are unsubstituted or substituted by C$_1$–C$_4$alkyl; C$_7$–C$_9$-phenylalkoxy which is unsubstituted or substituted on the phenyl ring by C$_1$–C$_4$alkyl; C$_{10}$–C$_{12}$naphthylalkoxy which is unsubstituted or substituted on the naphthyl ring by C$_1$–C$_4$alkyl; or the radicals R$_9$ and R$_{10}$ or the radicals R$_{10}$ and R$_{11}$ or the radicals R$_{11}$ and R$_{12}$ or the radicals R$_8$ and R$_{12}$ furthermore, together with the carbon atoms to which they are bonded, form a benzo ring which is unsubstituted or substituted by C$_1$–C$_4$alkyl, halogen or C$_1$–C$_4$alkoxy, R$_{13}$ is hydrogen, hydroxyl, halogen, nitro, cyano, CF$_3$, C$_1$–C$_{25}$alkyl, C$_2$–C$_{25}$alkyl which is interrupted by oxygen, sulfur or >N—R$_6$; C$_1$–C$_{25}$halogenoalkyl, C$_1$–C$_{18}$alkoxy, C$_2$–C$_{18}$alkoxy which is interrupted by oxygen, sulfur or >N—R$_6$; C$_1$–C$_{18}$alkylthio or C$_2$–C$_{24}$alkenyl;

R$_{14}$ and R$_{15}$ independently of one another are hydrogen, C$_1$–C$_{25}$alkyl, C$_2$–C$_{25}$alkyl which is interrupted by oxygen, sulfur or >N—R$_6$; C$_2$–C$_{24}$alkenyl, C$_5$–C$_{15}$cycloalkyl which is unsubstituted or substituted by C$_1$–C$_4$alkyl; phenyl or naphthyl which are unsubstituted or substituted by C$_1$–C$_4$alkyl, R$_{16}$ is hydrogen or C$_1$–C$_{18}$alkyl, R$_{17}$, R$_{18}$, R$_{19}$, R$_{20}$, R$_{21}$ and R$_{22}$ independently of one another are hydrogen or C$_1$–C$_{25}$alkyl, R$_{23}$ is hydrogen, C$_1$–C$_{25}$alkyl, C$_2$–C$_{25}$alkyl which is interrupted by oxygen, sulfur or >N—R$_6$; C$_2$–C$_{24}$alkenyl, C$_5$–C$_{15}$cycloalkyl which is unsubstituted or substituted by C$_1$–C$_4$alkyl; phenyl or naphthyl which are unsubstituted or substituted by C$_1$–C$_4$alkyl, R$_{24}$ and R$_{25}$ independently of one another are hydrogen, C$_1$–C$_{25}$alkyl, C$_1$–C$_{18}$alkoxy, —X$_2$—(CH$_2$)$_s$COR$_7$ or

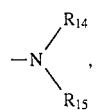

M is an r-valent metal cation,

X$_1$ is a direct bond, oxygen, sulfur, —NR$_{23}$—, C$_1$–C$_{18}$alkylene, C$_2$–C$_{18}$alkylene which is interrupted by oxygen, sulfur or >N—R$_6$, C$_2$–C$_{18}$alkenylene, C$_2$–C$_{18}$alkynylene, C$_2$–C$_{20}$alkylidene, C$_7$–C$_{20}$phenylalkylidene or C$_5$–C$_8$cycloalkylene, with the proviso that if m and n are 0, X$_1$ is other than oxygen and sulfur, X$_2$ is oxygen or —NR$_{23}$—, m and n independently of one another are an integer from 0 to 10, p is an integer from 0 to 4, r is 1,2 or 3, and s is an integer from 1 to 8, and excluding the titanium complexes of oxalic acid, citric acid, lactic acid, α-hydroxy-butyric acid, glyceric acid, with

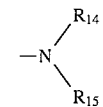

substituted aliphatic C$_1$–C$_{12}$carboxylic acid; o-phthalic acid, salicylic acid and glycine; and excluding the zirconium complexes of C$_3$–C$_{25}$carboxylic acid; naphthenic acid, malonic acid, succinic acid, adipic acid, maleic acid, phenylacetic acid, o-phthalic acid, cinnamic acid, benzoic acid, p-nitrobenzoic acid, salicylic acid and mandelic acid.

19. A compound according to claim 18, in which

R$_1$ is hydrogen, C$_1$–C$_{18}$alkyl, C$_2$–C$_{18}$alkyl which is interrupted by oxygen, sulfur or >N—R$_6$; C$_2$–C$_{18}$alkenyl, C$_4$–C$_{15}$cycloalkyl which is unsubstituted or substituted by C$_1$–C$_4$alkyl; C$_5$–C$_{12}$cycloalkenyl which is unsubstituted or substituted by C$_1$–C$_4$alkyl; C$_{13}$–C$_{26}$polycycloalkyl, C$_7$–C$_9$phenylalkyl, —COR$_7$, a 5- or 6- membered heterocyclic ring which is unsubstituted or substituted by C$_1$–C$_4$alkyl, C$_1$–C$_4$alkoxy, chlorine or carboxyl; a benzo-fused 5- or 6-membered heterocyclic ring which is unsubstituted or substituted by C$_1$–C$_4$alkyl, C$_1$–C$_4$alkoxy, chlorine or carboxyl; or R$_1$ furthermore is a radical of the formula II, III or IV

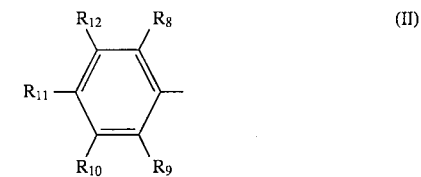

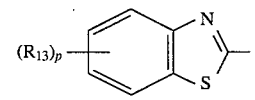

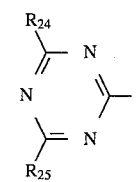

R$_2$, R$_3$, R$_4$ and R$_5$ independently of one another are hydrogen, hydroxyl, C$_1$–C$_{12}$alkoxy, C$_2$–C$_{12}$alkoxy which is interrupted by oxygen or sulfur;

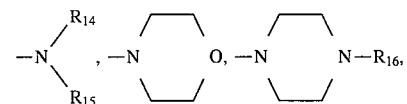

C$_1$–C$_{18}$alkyl, C$_2$–C$_{18}$alkyl which is interrupted by oxygen or sulfur; C$_2$–C$_{18}$alkenyl, C$_5$–C$_{15}$cycloalkyl, C$_5$–C$_{15}$cycloalkenyl, phenyl, naphthyl, C$_7$–C$_9$phenylalkyl, C$_{10}$–C$_{12}$naphthylalkyl or —COR$_7$, with the proviso that if one of the radicals R$_2$, R$_3$, R$_4$ or $R_5$ is hydroxyl,

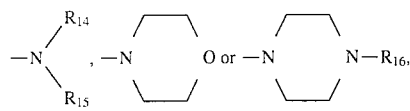

the other radical bonded to the same C atom is other than hydroxyl,

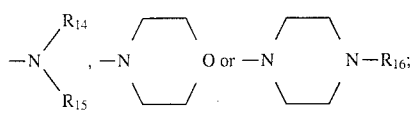

or $R_2$ and $R_3$ or $R_4$ and $R_5$ furthermore, together with the C atom to which they are bonded, form a $C_5$–$C_8$cycloalkylidene ring which is unsubstituted or substituted by $C_1$–$C_4$alkyl, $R_7$ is hydroxyl, $C_1$–$C_{12}$alkoxy, $C_2$–$C_{12}$alkoxy which is interrupted by oxygen or sulfur;

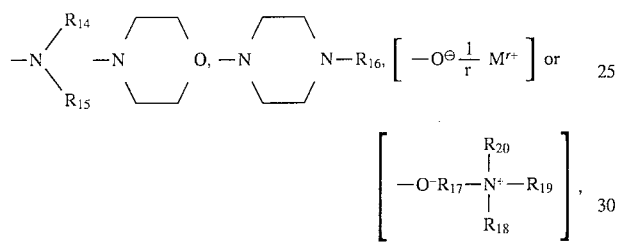

$R_8$, $R_9$, $R_{10}$, $R_{11}$ and $R_{12}$ independently of one another are hydrogen, hydroxyl, halogen, nitro,

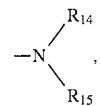

cyano, $CF_3$, —$COR_7$, $C_1$–$C_{18}$alkyl, $C_2$–$C_{18}$alkyl which is interrupted by by oxygen or sulfur; $C_1$–$C_{12}$alkylthio, $C_2$–$C_{18}$alkenyl, $C_5$–$C_{12}$cycloalkyl, $C_5$–$C_{12}$cycloalkenyl, phenyl, naphthyl, $C_7$–$C_9$-phenylalkyl, $C_{10}$–$C_{12}$naphthylalkyl, phenoxy, naphthoxy, $C_7$–$C_9$phenylalkoxy or $C_{10}$–$C_{12}$naphthylalkoxy; or the radicals $R_9$ and $R_{10}$ or the radicals $R_{10}$ and $R_{11}$ or the radicals $R_{11}$ and $R_{12}$ or the radicals $R_8$ and $R_{12}$ furthermore, together with the carbon atoms to which they are bonded, form a benzo ring which is unsubstituted or substituted by $C_1$–$C_4$alkyl or chlorine, $R_{13}$ is hydrogen, hydroxyl, halogen, nitro, cyano, $CF_3$, $C_1$–$C_{18}$alkyl, $C_2$–$C_{18}$alkyl which is interrupted by oxygen or sulfur; $C_1$–$C_{18}$halogenoalkyl, $C_1$–$C_{12}$alkoxy, $C_2$–$C_{12}$alkoxy which is interrupted by oxygen or sulfur; $C_1$–$C_{12}$alkylthio or $C_2$–$C_{18}$alkenyl, $R_{14}$ and $R_{15}$ independently of one another are hydrogen, $C_1$–$C_{18}$alkyl, $C_2$–$C_{18}$alkyl which is interrupted by oxygen or sulfur; $C_2$–$C_{18}$alkenyl, $C_5$–$C_{12}$cycloalkyl, phenyl or naphthyl, $R_{16}$ is hydrogen or $C_1$–$C_{12}$alkyl, $R_{17}$, $R_{18}$, $R_{19}$, $R_{20}$, $R_{21}$ and $R_{22}$ independently of one another are hydrogen or $C_1$–$C_{18}$alkyl, $R_{23}$ is hydrogen, $C_1$–$C_{18}$alkyl, $C_2$–$C_{18}$alkyl which is interrupted by oxygen or sulfur; $C_2$–$C_{18}$alkenyl, $C_5$–$C_{12}$cycloalkyl, phenyl or naphthyl, $R_{24}$ and $R_{25}$ independently of one another are hydrogen, $C_1$–$C_{18}$alkyl, $C_1$–$C_{12}$alkoxy, —$X_2$—$(CH_2)_sCOR_7$ or

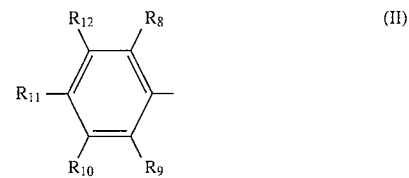

$X_1$ is a direct bond, oxygen, sulfur, —$NR_{23}$—, $C_1$–$C_{12}$alkylene, $C_2$–$C_{12}$alkylene which is interrupted by oxygen or sulfur; $C_2$–$C_{12}$alkenylene, $C_2$–$C_{12}$alkynylene, $C_2$–$C_{16}$alkylidene, $C_7$–$C_{16}$phenylalkylidene or $C_5$–$C_8$cycloalkylene, with the proviso that if m and n are 0, $X_1$ is other than oxygen and sulfur, $X_2$ is —$NR_{23}$—, p is 0, 1 or 2, and s is an integer from 2 to 7.

20. A compound according to claim 18, in which $R_1$ is hydrogen, $C_1$–$C_{12}$alkyl, $C_3$–$C_{12}$alkyl which is interrupted by oxygen; $C_2$–$C_{12}$alkenyl, $C_4$–$C_{15}$cycloalkyl, $C_5$–$C_8$cycloalkenyl, $C_{13}$–$C_{26}$polycycloalkyl, benzyl, —$COR_7$, or thienyl, tetrahydrofuranyl, furyl, pyrrolidinyl, pyrrolyl, thiazolyl, isothiazolyl, triazolyl, tetrazolyl, oxazolyl, isoxazolyl, pyridyl, piperidinyl, pyrazinyl, piperazinyl or triazinyl which are unsubstituted or substituted by $C_1$–$C_4$alkyl, $C_1$–$C_4$alkoxy, chlorine or carboxyl or benzo-fused; or $R_1$ furthermore is a radical of the formula II, III or IV

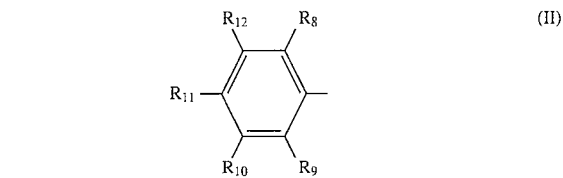 (II)

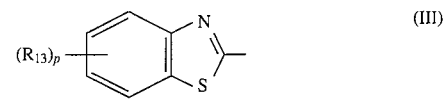 (III)

 (IV)

$R_7$ is hydroxyl, $C_1$–$C_{10}$-alkoxy, $C_2$–$C_{12}$alkoxy which is interrupted by oxygen;

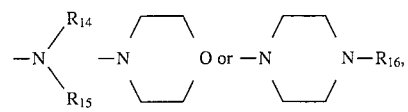

$R_8$, $R_9$, $R_{10}$, $R_{11}$ and $R_{12}$ independently of one another are hydrogen, hydroxyl, chlorine, nitro,

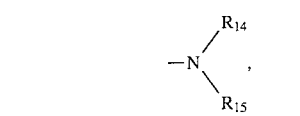

—$COR_7$, $C_1$–$C_{12}$alkyl, $C_2$–$C_{16}$alkyl which is interrupted by oxygen; $C_1$–$C_{12}$halogenoalkyl, $C_1$–$C_{12}$alkoxy, $C_2$–$C_{12}$alkoxy which is interrupted by oxygen; $C_2$-$C_{12}$alkenyl, $C_5$-$C_9$cycloalkyl, $C_5$-$C_9$cycloalkenyl, phenyl, naphthyl, $C_7$-$C_9$phenylalkyl, $C_{10}$-$C_{12}$naphthylalkyl, phenoxy or $C_7$-$C_9$phenylalkoxy; or the radicals $R_9$ and $R_{10}$ or the radicals $R_{10}$ and $R_{11}$ furthermore, together with the carbon atoms to which they are bonded, form a benzo ring, $R_{13}$ is hydrogen, hydroxyl, chlorine, nitro, $C_1$-$C_{12}$alkyl, $C_2$-$C_{12}$alkyl which is interrupted by oxygen; $C_1$-$C_{10}$alkoxy or $C_2$-$C_{10}$alkoxy which is interrupted by oxygen, $R_{14}$ and $R_{15}$ independently of one another are hydrogen, $C_1$-$C_{12}$alkyl, $C_2$-$C_{12}$alkyl which is interrupted by oxygen; $C_5$-$C_9$cycloalkyl or phenyl, $R_{16}$ is hydrogen or $C_1$-$C_8$alkyl, $R_{23}$ is hydrogen, $C_1$-$C_{12}$alkyl, $C_3$-$C_{12}$alkyl which is interrupted by oxygen; $C_2$-$C_{12}$alkenyl, $C_5$-$C_9$cycloalkyl or phenyl, $R_{24}$ and $R_{25}$ independently of one another are hydrogen or —$X_2$—$(CH_2)_s COR_7$ or

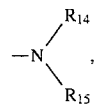

$X_1$ is a direct bond, oxygen, sulfur, —$NR_{23}$—, $C_1$-$C_8$alkylene, $C_2$-$C_8$alkenylene, $C_2$-$C_8$-alkynylene, $C_2$-$C_{12}$alkylidene, $C_7$-$C_{12}$phenylalkylidene or $C_5$-$C_8$cycloalkylene, with the proviso that if m and n are 0, $X_1$ is other than oxygen and sulfur, $X_2$ is —$NR_{23}$—, p is 0 or 1, and s is an integer from 3 to 6.

21. A compound according to claim 18, in which $R_2$, $R_3$, $R_4$ and $R_5$ independently of one another are hydrogen, hydroxyl, $C_1$-$C_{10}$alkoxy, $C_2$-$C_{12}$alkoxy which is interrupted by oxygen;

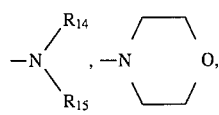

$C_1$-$C_{12}$alkyl, $C_2$-$C_{18}$alkyl which is interrupted by oxygen; $C_2$-$C_{12}$alkenyl, $C_5$-$C_9$cycloalkyl, $C_5$-$C_9$cycloalkenyl, phenyl, naphthyl, $C_7$-$C_9$phenylalkyl or —$COR_7$, with the proviso that if one of the radicals $R_2$, $R_3$, $R_4$ or $R_5$ is hydroxyl,

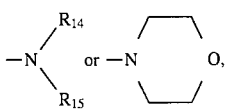

the other radical bonded to the same C atom is other than hydroxyl,

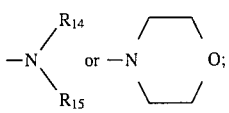

or $R_2$ and $R_3$ or $R_4$ and $R_5$ furthermore, together with the C atom to which they are bonded, form a $C_5$-$C_8$cycloalkylidene ring which is unsubstituted or substituted by $C_1$-$C_4$alkyl, and $R_7$ is hydroxyl, $C_1$-$C_{10}$alkoxy, $C_2$-$C_{12}$alkoxy interrupted by oxygen;

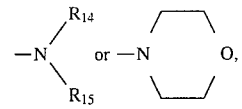

and $R_{14}$ and $R_{15}$ independently of one another are hydrogen, $C_1$-$C_{12}$alkyl, $C_2$-$C_{12}$alkyl which is interrupted by oxygen; $C_5$-$C_9$cycloalkyl or phenyl.

22. A compound according to claim 18, in which $R_2$, $R_3$, $R_4$ and $R_5$ independently of one another are hydrogen, hydroxyl, $C_1$-$C_{10}$alkoxy,

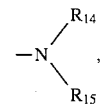

$C_1$-$C_{12}$alkyl, $C_2$-$C_{12}$alkenyl, $C_5$-$C_9$cycloalkenyl, with the proviso that if one of the radicals $R_2$, $R_3$, $R_4$ or $R_5$ is hydroxyl or

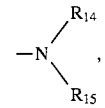

the other radical bonded to the same C atom is other than hydroxyl or

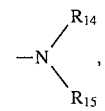

and $R_{14}$ and $R_{15}$ independently of one another are hydrogen or $C_1$-$C_8$alkyl.

23. A compound according to claim 18, in which $R_1$ is hydrogen, $C_1$-$C_{12}$alkyl, $C_2$-$C_{12}$alkenyl, $C_4$-$C_{15}$cycloalkyl, $C_{13}$-$C_{26}$polycycloalkyl, benzyl, —$COR_7$, pyrrolidinyl which is unsubstituted or substituted by $C_1$-$C_4$alkyl, $C_1$-$C_4$alkoxy or chlorine; or $R_1$ furthermore is a radical of the formula II or III

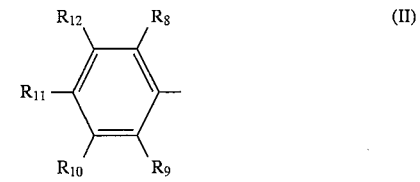

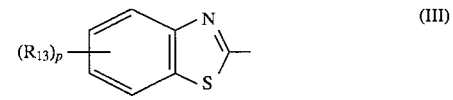

$R_7$ is hydroxyl or $C_1$-$C_{10}$alkoxy, $R_8$, $R_9$, $R_{10}$, $R_{11}$ and $R_{12}$ independently of one another are hydrogen, hydroxyl, chlorine, nitro, —$COR_7$, $C_1$-$C_8$alkyl, $C_1$-$C_4$alkoxy or cyclohexyl; or the radicals $R_9$ and $R_{10}$ or the radicals $R_{10}$ and $R_{11}$ furthermore, together with the carbon atoms to which they are bonded, form a benzo ring, $R_{13}$ is hydrogen, $C_1$-$C_4$alkyl, chlorine or $C_1$-$C_4$alkoxy, $R_{23}$ is hydrogen, $C_1$-$C_8$alkyl or phenyl, $X_1$ is a direct bond, oxygen, sulfur, —$NR_{23}$— or $C_2$-$C_4$alkenylene, with the proviso that if m and n are 0, $X_1$ is other than oxygen and sulfur, and p is 0 or 1.

24. A compound according to claim 18, in which $R_1$ is hydrogen, $C_4$-$C_{15}$cycloalkyl, $C_{13}$-$C_{26}$polycycloalkyl or —$COR_7$; or $R_1$ furthermore is a radical of the formula II or III

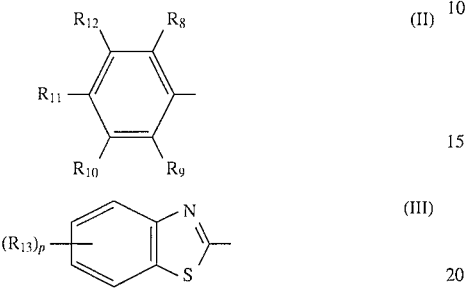

$R_2$, $R_3$, $R_4$ and $R_5$ independently of one another are hydrogen, hydroxyl or —$COR_7$, with the proviso that if one of the radicals $R_2$, $R_3$, $R_4$ or $R_5$ is hydroxyl, the other radical bonded to the same C atom is other than hydroxyl, $R_7$ is hydroxyl, $R_8$ is hydrogen, hydroxyl or —$COR_7$, $R_9$ is hydrogen, $R_{10}$ is hydrogen, $C_1$-$C_4$alkyl or nitro, $R_{11}$ is hydrogen, methyl, nitro or chlorine, or the radicals $R_{10}$ and $R_{11}$, together with the carbon atoms to which they are bonded, form a benzo ring, $R_{12}$ is hydrogen, $C_1$-$C_4$alkyl or —$COR_7$, $R_{23}$ is hydrogen, $X_1$ is a direct bond, oxygen, sulfur, —$NR_{23}$—or vinylene, with the proviso that if m and n are 0, $X_1$ is other than oxygen and sulfur, m is an integer from 0 to 8, n is an integer from 0 to 8, and p is 0.

* * * * *